United States Patent
Agnew et al.

(10) Patent No.: US 8,716,033 B2
(45) Date of Patent: May 6, 2014

(54) OLIGOSACCHARIDE MODIFICATION AND LABELING OF PROTEINS

(75) Inventors: Brian Agnew, Eugene, OR (US); Schuyler B. Corry, Eugene, OR (US); Kyle R. Gee, Springfield, OR (US)

(73) Assignee: Life Technologies Corporation, Carlsbad, CA (US)

( * ) Notice: Subject to any disclaimer, the term of this patent is extended or adjusted under 35 U.S.C. 154(b) by 1818 days.

(21) Appl. No.: 11/674,136

(22) Filed: Feb. 12, 2007

(65) Prior Publication Data

US 2007/0190597 A1    Aug. 16, 2007

Related U.S. Application Data

(60) Provisional application No. 60/804,640, filed on Jun. 13, 2006, provisional application No. 60/772,221, filed on Feb. 10, 2006.

(51) Int. Cl.
*G01N 33/532* (2006.01)
*G01N 33/534* (2006.01)
*G01N 33/533* (2006.01)
*C07K 1/10* (2006.01)

(52) U.S. Cl.
USPC ........... 436/544; 436/534; 436/533; 530/402; 530/405

(58) Field of Classification Search
None
See application file for complete search history.

(56) References Cited

U.S. PATENT DOCUMENTS

| | | | |
|---|---|---|---|
| 4,196,265 A | 4/1980 | Koprowski et al. | |
| 4,384,042 A | 5/1983 | Miike et al. | |
| 4,520,110 A | 5/1985 | Stryer et al. | |
| 4,542,104 A | 9/1985 | Stryer et al. | |
| 4,603,209 A | 7/1986 | Tsien et al. | |
| 4,711,955 A | 12/1987 | Ward et al. | |
| 4,714,763 A | 12/1987 | Theodoropulos | |
| 4,774,339 A | 9/1988 | Haugland et al. | |
| 4,810,636 A | 3/1989 | Corey | |
| 4,812,409 A | 3/1989 | Babb et al. | |
| 4,816,567 A | 3/1989 | Cabilly et al. | |
| 4,849,362 A | 7/1989 | Demarinis et al. | |
| 4,859,582 A | 8/1989 | Stryer et al. | |
| 4,945,171 A | 7/1990 | Haugland et al. | |
| 4,981,977 A | 1/1991 | Southwick et al. | |
| 5,047,519 A | 9/1991 | Hobbs, Jr. et al. | |
| 5,055,556 A | 10/1991 | Stryer et al. | |
| 5,132,432 A | 7/1992 | Haugland et al. | |

(Continued)

FOREIGN PATENT DOCUMENTS

EP    171496    2/1986
EP    184187    6/1986

(Continued)

OTHER PUBLICATIONS

Breinbauer et al. Azide-alkyne coupling: a powerful reaction for bioconjugate chemistry. ChemBioChem 2003, vol. 5, pp. 1147-1149.*

(Continued)

*Primary Examiner* — Shafiqul Haq
(74) *Attorney, Agent, or Firm* — Life Technologies Corporation

(57) ABSTRACT

The present invention generally relates to methods of functionalizing proteins, particularly antibodies, at oligosaccharide linkages, methods of humanizing antibodies by modifying glycosylation, as well as to novel antibodies linked to modified oligosaccharides. The invention further relates to kits that may be used to produce the antibodies of the invention.

10 Claims, 22 Drawing Sheets

(56) References Cited

U.S. PATENT DOCUMENTS

| | | |
|---|---|---|
| 5,187,288 A | 2/1993 | Kang et al. |
| 5,196,306 A | 3/1993 | Bobrow et al. |
| 5,208,148 A | 5/1993 | Haugland et al. |
| 5,225,539 A | 7/1993 | Winter |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,133 A | 12/1993 | Narula |
| 5,279,954 A | 1/1994 | Wagner et al. |
| 5,316,906 A | 5/1994 | Haugland et al. |
| 5,362,628 A | 11/1994 | Haugland et al. |
| 5,442,045 A | 8/1995 | Haugland et al. |
| 5,443,986 A | 8/1995 | Haughland et al. |
| 5,451,343 A | 9/1995 | Neckers et al. |
| 5,459,276 A | 10/1995 | Kuhn et al. |
| 5,478,741 A | 12/1995 | Maret et al. |
| 5,486,616 A | 1/1996 | Waggoner et al. |
| 5,501,980 A | 3/1996 | Katerinopoulos et al. |
| 5,545,806 A | 8/1996 | Lonberg et al. |
| 5,569,587 A | 10/1996 | Waggoner |
| 5,569,766 A | 10/1996 | Waggoner et al. |
| 5,569,825 A | 10/1996 | Lonberg et al. |
| 5,576,424 A | 11/1996 | Mao et al. |
| 5,583,001 A | 12/1996 | Bobrow et al. |
| 5,625,126 A | 4/1997 | Lonberg et al. |
| 5,627,027 A | 5/1997 | Waggoner |
| 5,633,425 A | 5/1997 | Lonberg et al. |
| 5,661,016 A | 8/1997 | Lonberg et al. |
| 5,696,157 A | 12/1997 | Wang et al. |
| 5,731,158 A | 3/1998 | Bobrow et al. |
| 5,773,236 A | 6/1998 | Diwu et al. |
| 5,798,276 A | 8/1998 | Haugland et al. |
| 5,808,044 A | 9/1998 | Brush et al. |
| 5,830,912 A | 11/1998 | Gee et al. |
| 5,846,737 A | 12/1998 | Kang |
| 5,858,731 A | 1/1999 | Sorge et al. |
| 5,874,532 A | 2/1999 | Pieken et al. |
| 5,877,310 A | 3/1999 | Reddington et al. |
| 5,948,386 A | 9/1999 | Katti |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,127,134 A | 10/2000 | Minden et al. |
| 6,130,094 A | 10/2000 | Waggoner et al. |
| 6,130,101 A | 10/2000 | Mao et al. |
| 6,133,445 A | 10/2000 | Waggoner et al. |
| 6,162,931 A | 12/2000 | Gee et al. |
| 6,339,392 B1 | 1/2002 | Ashihara et al. |
| 6,562,632 B1 | 5/2003 | Szalecki et al. |
| 6,570,040 B2 | 5/2003 | Saxon et al. |
| 6,664,047 B1 | 12/2003 | Haugland et al. |
| 6,716,979 B2 | 4/2004 | Diwu et al. |
| 6,737,236 B1 | 5/2004 | Pieken et al. |
| 6,936,701 B2 | 8/2005 | Bertozzi et al. |
| 6,974,873 B2 | 12/2005 | Leung et al. |
| 6,977,305 B2 | 12/2005 | Leung et al. |
| 7,052,843 B2 | 5/2006 | Li et al. |
| 7,070,941 B2 | 7/2006 | Zhao et al. |
| 7,122,703 B2 | 10/2006 | Saxon et al. |
| 7,265,085 B2 * | 9/2007 | DeFrees et al. .................. 514/8 |
| 7,332,355 B2 * | 2/2008 | Hsieh-Wilson et al. ...... 436/544 |
| 7,375,234 B2 | 5/2008 | Sharpless et al. |
| 7,427,678 B2 | 9/2008 | Pieken et al. |
| 7,763,736 B2 | 7/2010 | Sharpless et al. |
| 2002/0012989 A1 | 1/2002 | Ledbetter et al. |
| 2003/0049721 A1 | 3/2003 | Bertozzi et al. |
| 2003/0073149 A1 | 4/2003 | Archer et al. |
| 2003/0211579 A1 | 11/2003 | Van Ness et al. |
| 2003/0219876 A1 | 11/2003 | Ledbetter et al. |
| 2004/0067497 A1 | 4/2004 | Li et al. |
| 2004/0142856 A1 | 7/2004 | DeFrees et al. |
| 2004/0235076 A1 | 11/2004 | Liu et al. |
| 2005/0032081 A1 * | 2/2005 | Ju et al. ............................ 435/6 |
| 2005/0106627 A1 | 5/2005 | Zhao et al. |
| 2005/0130235 A1 | 6/2005 | Hsieh-Wilson et al. |
| 2005/0222427 A1 | 10/2005 | Sharpless et al. |
| 2006/0205041 A1 | 9/2006 | Frye et al. |
| 2007/0249014 A1 | 10/2007 | Agnew et al. |
| 2008/0108557 A1 * | 5/2008 | Behrens et al. .................. 514/8 |
| 2009/0215635 A1 | 8/2009 | Carell et al. |
| 2009/0240030 A1 | 9/2009 | Ju et al. |
| 2010/0261181 A1 | 10/2010 | Agnew et al. |

FOREIGN PATENT DOCUMENTS

| | | |
|---|---|---|
| EP | 125023 | 6/1991 |
| EP | 1065250 | 12/2004 |
| JP | 2005-314382 | 11/2005 |
| WO | WO-86/01533 | 3/1986 |
| WO | 96/09316 | 3/1996 |
| WO | 96/20289 | 7/1996 |
| WO | 96/34984 | 11/1996 |
| WO | WO-97/40104 | 10/1997 |
| WO | 98/30575 | 7/1998 |
| WO | WO-99/51702 | 10/1999 |
| WO | WO-01/21624 | 3/2001 |
| WO | WO-01/68565 | 9/2001 |
| WO | WO-02/26891 | 4/2002 |
| WO | 03/101972 A1 | 12/2003 |
| WO | 2004/018497 | 3/2004 |
| WO | 2004033651 | 4/2004 |
| WO | WO-2004/033651 | 4/2004 |
| WO | WO-2004/063344 | 7/2004 |
| WO | WO-2005/042504 | 5/2005 |
| WO | WO-2005/050226 A1 | 6/2005 |
| WO | WO-2005/075993 A1 | 8/2005 |
| WO | 2006/038184 | 4/2006 |
| WO | 2006/117161 | 11/2006 |
| WO | WO-2007095506 | 8/2007 |
| WO | WO-2008/029281 | 3/2008 |

OTHER PUBLICATIONS 07756886.3, "Extended EP Search Report mailed Nov. 28, 2012", 1-6.

Anumula, et al., "Advances in fluorescence derivatization methods for high-performance liquid chromatographic analysis of glycoprotein carbohydrates", *Analytical Biochemistry*, Academic Press, vol. 350, 2006, pp. 1-23.

Camarero, J A., "New developments for the site-specific attachment of protein to surfaces", *Biophysical Reviews and Letters*, 2005, 1-28.

Laughlin, S. et al., "Metabolic Labeling of Glycans with Azido Sugars for Visualization and Glycoproteomics", *Methods in Enzymology*, Academic Press, US, vol. 415, 2006, pp. 230-250.

Luchansky, S. et al., "Constructing Azide-Labeled Cell Surfaces Using Polysaccharide Biosynthetic Pathway", *Methods in Enzymology*, vol. 362, 2003, pp. 249-272.

Soellner, Matthew B. et al., "Site-Specific Protein Immobilization by Staudinger Ligation", *J. Amer. Chem. Soc.*, vol. 125, 2003, 11790-11791.

*Stratagene Catalog*, 1988, p. 39.

EP 08729780.0 Extended European Search Report mailed Mar. 15, 2010.

EP 08729780.0 Supplementary European Search Report mailed on Apr. 23, 2010.

EP 10153793.4 Extended European Search Report mailed Jul. 12, 2010.

Anonymous, "Telomerase PCR ELISA. For fast and sensitive detection of telomerase activity ", *Biochemica*, [Online] Jan. 1, 1996, pp. 7-8, vol. 1996, No. 4,, 1996, 7-8.

Anonymous, "TRAPeze telomerase detection kit. S770", XP7913582, 2005, 43 pp.

Antos, J. M. et al., "Transition metal catalyzed methods for site-selective protein modification", *Current Opinion in Chemical Biology*; vol. 10(3), Jun. 1, 2006, 253-262.

Bertozzi, et al., "A Strain-Promoted [3+2] Azide-Alkyne Cycloaddition for Covalent Modification of Biomolecules in Living Systems.", *J. Am. Chem. Soc.*, 126, 2004, 15046-15047.

(56) References Cited

OTHER PUBLICATIONS

Fukui, T., "Addition of potato recovered from potato starch factory waste effluents for bread", *Internet Citation*, 25(1), Jan. 1, 1978, 43-46.
Helenius, Ari et al., "Intracellular Functions of N-Linked Glycans", *Science*, vol. 291, 2001, 2364-2369.
Langenhan, J. M. et al., "Recent Carbohydrate-based chemoeslective ligation applications", *Current organics systhesis*, 2(1), Jan. 2005, 59-81.
Lee., B. et al., "Interaction of Psoralen-Derivatized Oligodeoxyribonucleoside Methylphosphonates with single-Stranded DNA", *Biochemistry*, 27, 1988, 3197-3203.
Murakami, N. et al., "Studies on Cardiac Ingrediets of Plants. VII: Chemical Transformation of Proscillaridin by Means of the Diels-Alder Reaction and Biological Activities of its Derivatives", *Chem. Pharm. Bull. 39 (8)*, 1991, 1962-1966.
PCT/US08/053870, International Preliminary Report on Patentability mailed Jul. 31, 2008.
PCT/US08/053870, Written Opinion mailed Jul. 31, 2008.
Pei, Y. et al., "Post-Modification of Peptoid Side Chains: [3+2] Cycloaddition of Nitrole Oxides with Alkenes and Alkynes on the Solid-Phase", *Tetrahedron Letters*, vol. 35, No. 32, 1994, 5825-5828.
Rodionov, V. et al., "Mechanism of the Ligand-Free Cu-Catalyzed Azide-Alkyne Cycloaddition Reaction", *Angew. Chem. Int. Ed.*, vol. 44, 2005, 2210-2215.
Speers, Anna E. et al., "Profiling Enzyme Activities in Vivo Using Click Chemistry Methods", *Chemistry & Biology*, vol. 11, Apr. 1, 2004, 535-546.
Wang, Q. et al., "Bioconjugation by Copper (I)-Catalyzed Azide0Alkyne [3+2] Cycloaddition", *J. Am. Chem. Soc. 125*, 2003, 3192-3193.
Agard, N., "A Strain-Promoted [3+2] Azide-Alkyne Cycloaddition for Covalent Modification of Biomolecules in Living Systems", *J. Am. Chem. Soc.*, 2004, pp. 15046-15047.
Chan, T. et al., "Polytriazoles as Copper(I)-Stabilizing Ligands in Catalysis", *Organic Letters*, vol. 6, No. 17, 2004, pp. 2853-2855.
EP 13162103.9, "Extended European Search Report", 2013, pp. 1-9.
Gupta, S. et al., "Virus-glycopolymer conjugates by copper(I) catalysis of atom transfer radical polymerization and azide-alkyne cycloaddition", *The Royal Society of Chemistry*, Chem. Commun., 2005, pp. 4315-4317.
Hang, H. et al., "A metabolic labeling approach toward proteomic analysis of mucin-type 0-linked glycosylation", *Proceedings of the National Academy of Sciences of the USA*, vol. 100, No. 25, 2003, 14846-14851.
Hang, H. et al., "Probing Glycosyltransferase Activities with the Staudinger Ligation", vol. 126, No. 1, 2004, pp. 6-7.
Hang, H. et al., "The chemistry and biology of mucin-type 0-linked glycosylation", *Bioorganic & Medicinal Chemistry*, 13, 2005, 5021-5034.
Maciej, A. et al., "Identification of phosphopeptides by chemical modification with an isotopic tag and ion trap mass spectrometry", *Rapid Communications in Mass Spectrometry*, vol. 16, 2002, pp. 999-1001.
Mattila, K. et al., "Derivatization of phosphopeptides with mercapto- and amino-functionalized conjugate groups by phosphate elimination and subsequent Michael addition", *Org. Biomol. Chem.*, vol. 3, 2005, pp. 3039-3044.
Pohl, N. et al., "Cellular Addresses: Step One in Creating a Glycocode", *Chemistry & Biology*, vol. 11, 2004, pp. 891-892.
Speers, A., "Profiling Enzyme Activities in Vivo Using Click Chemistry Methods", *Chemistry & Biology*, vol. 11, 2004, pp. 535-546.
Sun, X. et al., "Carbohydrate and Protein Immobilization onto Solid Surfaces by Sequential Deils-Alder and Azide-Alkyne Cycloadditions", *American Chemical Society*, Bioconjugate Chem., vol. 17, 2006, pp. 52-57.
Wang, Q. et al., "Advances in 1,3-Dipolar Cycloaddition Reaction of Azides and Alkynes-A Prototype of "Click" Chemistry", *Letters in Organic Chemistry*, vol. 2, 2005, pp. 293-301.
Wang, Q. et al., "Bioconjugation by Copper(I)-Catalyzed Azide-Alkyne [3 +2] Cycloaddition", *J. Am. Chem. Soc.*, vol. 125, 2003, pp. 3192-3193.
Weckwerth, W. et al., "Comparative quantification and identification of phosphoproteins using stable isotope labeling and liquid chromatography/mass spectrometry", *Rapid Communications in Mass Spectrometry*, vol. 14, 2000, pp. 1677-1681.
EP 07825657.5, Extended European Search Report mailed Aug. 23, 2010.
EP 07825657.5, Office Action mailed Apr. 6, 2011.
U.S. Appl. No. 11/674,140, Office Action mailed Mar. 22, 2010.
U.S. Appl. No. 11/674,140, Office Action mailed Sep. 29, 2009.
U.S. Appl. No. 11/674,140, Response to Sep. 29, 2009 Office Action filed Dec. 28, 2009.
U.S. Appl. No. 11/674,140, Office Action Mailed on Oct. 19, 2010.
Agard et al., *J. Am. Chem Soc*, vol. 126(46):15046-15047 (2004).
Beidler et al., *J. Immunol.* 141(11):4053-4060 (1988).
Better et al., *Science* 240:1041-1043 (1988).
Berliner, *Biochemistry* vol. 21, No. 25 1982, 6340-6343.
Bouizar et al., *Eur. J. Biochem.* 155(1):141-147 (1986).
Browning et al., *J. Immunol.* 143(6):1859-1867 (1989).
Capila et al., *Angew. Chem. Int. Ed.* 41:390-412 (2002).
Comer et al., *Anal. Biochem.* 293:169-177 (2001).
Do, et al. *J. Biol. Chem.* vol. 270, No. 31 1995, 18447-18451.
Dube et al., *Current Opinion in Chemical Biology* 7:616-625 (2003).
Gastinel, *The EMBO Journal* vol. 18, No. 13 1999, 3546-3557.
Gorevic et al., *Methods in Enzymology* 116:3-25 (1985).
Gupta et al., *Chem. Commun.* 34:4315-4317 (2005).
Hang et al., *PNAS* 100(25):14846-14851 (2003).
Hang et al., *J. Am. Chem. Soc.* 126(1):6-7 (2004).
Hang et al., *Bioorganic & Medicinal Chemistry* 13(7):5021-5034 (2005).
Haugland, R., Handbook of Fluorescent Probes and Research Products, Ninth Edition, Molecular Probes, Inc. (CD-ROM: ISBN 0-9710636-3-X), (2002).
Haugland, R., The Molecular Probes Handbook: A Guide to Fluorescent Probes and Labeling Technologies, Eleventh Edition, Molecular Probes, Inc. (CD-ROM: ISBN 978-0-9829279-0-8), (2010).
Henderson et al., *Advances in Immunology* 62:217-256 (1996).
Jespers et al., *Nature Biotechnology* 12(9):899-903 (1994).
Jones et al., *Nature* 321:522-525 (1986).
Joshi et al. *J. Biol. Chem.* 265(24):14518-14525 (1990).
Jung et al., *Biochimica et Biophysica Acta*, 761(2):152-162 (1983).
Khidekel et al., *J. Am. Chem. Soc.* 125(52):16162-16163 (2003).
Kiick et al., *PNAS* 99(1):19-24 (2002).
Kolb et al., *Angew. Chem. Int. Ed.* 40:2004-2021 (2001).
Lasky, L. A., *Annu. Rev. Biochem.* 64:113-139 (1995).
Lazarevic et al., *Carbohydrate Research* 337:2187-2194 (2002).
Lewis et al., *Angew. Chem. Int. Ed.* 41(6):1053-1057 (2002).
Liu et al., *PNAS* 84(10):3439-3443 (1987).
Liu et al., *J. Immunol.* 139(10):3521-3526 (1987).
Lonberg et al., *Intern. Rev. Immunol.* 13(1):65-93 (1995).
Losey et al., *Chemistry & Biology* 9:1305-1314 (2002).
Luchansky, et al. *Biochemistry* 2004; vol. 43, 12358-12366.
Martin et al., *Nature Medicine* 11(2):228-232 (2005).
Morrison, S. L., *Science* 229:1202-1207 (1985).
Morrison, S. L. *Science* 229 1985, 1202-1207.
Nishimura et al., *Cancer Research* 47:999-1005 (1987).
Oi et al., *BioTechniques* 4(3):214-221 (1986).
Park et al., *J. Biol. Chem.* 261(1):205-210(1986).
Pauling, L. *J. Am. Chem. Soc.* vol. 59, No. 1 1937, 13-20.
PCT/IB07/003472, International Search Report mailed Dec. 2, 2009.
PCT/IB07/03472, International Search report mailed on Jul. 29, 2009.
PCT/US07/62006, International Preliminary Report on Patentability mailed Jul. 5, 2007.
PCT/US07/62006, International Search Report mailed Jul. 5, 2007.
PCT/US07/62006, Written Opinion mailed Jul. 5, 2007.
Pohl et al., *Chemistry & Biology* 11:891-892 (2004).
Ramakrishnan, *J. Biol. Chem.* vol. 277, No. 23 2002, 20833-20839.
Ramakrishnan, *J. Biol. Chem.* vol. 276, No. 40 2001, 37665-37671.
Roquemore et al., *Methods in Enzymology* 230:443-460 (1994).

(56) References Cited

OTHER PUBLICATIONS

Rudd et al., *Science* 291:2370-2376 (2001).
Saxon et al., *Science* 287(5460):2007-2010 (2000).
Saxon et al., *J. Am. Chem. Soc.* 124(50):14893-14902 (2002).
Shaw et al., *J. Natl. Cancer Inst.* 80(19):1553-1559 (1988).
Snow et al., *J. Cell Biol.* 104:1143-1156 (1987).
Staudinger et al., *Helvetica Chimica Acta.* 2(1):635-646 (1919).
Sun et al., *Bioconjugate Chem.*,17(1):52-57 (2006).
Sun et al., *PNAS* 84:214-218 (1987).
Takeuchi et al., *J. Biol. Chem*, 265(21):12127-12130 (1990).
Tamura et al., *Analytical Biochemistry* 216(2):335-344 (1994).
Varki, A., *Glycobiology* 3(2):97-130 (1993).
Verhoeyen et al., *Science* 239:1534-1536 (1988).
Vocadlo, *PNAS 2003*; vol. 100(16), 9116-9121.
Wang et al., *J. Am. Chem. Soc.* 125(11):3192-3193 (2003).
Wells et al., *Science* 291:2376-2378 (2001).
Wood et al., *Nature* 314:446-449 (1985).
Zachara et al., *Chem. Rev.* 102(2):431-438 (2002).
Zarling et al., *J. Immunol.* 124(2):913-920 (1980).

\* cited by examiner

TAMRA alkyne Label  SYPRO Ruby Gel Stain

TAMRA alkyne Label  SYPRO Ruby stain

A.

B.

OLIGOSACCHARIDE MODIFICATION AND LABELING OF PROTEINS

This application claims priority to U.S. Provisional Application No. 60/772,221, filed Feb. 10, 2006 and U.S. Provisional Application No. 60/804,640, filed Jun. 13, 2006, the contents of which are incorporated by reference as if set forth fully herein.

FIELD OF THE INVENTION

The invention generally relates to methods of labeling proteins at novel oligosaccharide linkages, methods of humanizing antibodies by modifying glycosylation, as well as to novel antibodies linked to modified oligosaccharides.

BACKGROUND

Isolated or synthesized proteins and antibodies, such as IgGs, are used therapeutically and for diagnostic and research purposes. By labeling antibodies with detectable labels, such as, for example, fluorophores, antibodies can be used to specifically detect target biological molecules or cells. Antibodies may also be tagged with binding reagents, such as, for example, biotin, so that they may be used to specifically bind target biological molecules or cells, followed by purification of the biological molecule or cell by using a reagent that binds to the tagged antibody, for example, streptavidin. Antibodies have generally been labeled at cysteine or lysine residues, which may often be present in the Fab, or binding portion of the antibody. Adding tags or labels in this region may disrupt or at least alter the binding properties of the antibody. Further, it is often difficult to quantitate the number of labeled molecules attached to each antibody.

Therapeutic monoclonal antibodies (Mabs) have become indispensable drugs to combat cancer, rheumatoid arthritis, macular degeneration, and other diseases or conditions. However, antibodies generated in non-human cell lines may have antigenic features recognized as foreign by the human immune system, limiting the antibodies' half-life and efficacy. Incorporating human IgG sequences into transgenic mice has reduced, but not eliminated, immunogenicity problems. Besides the protein sequence, the nature of the oligosaccharides attached to the IgG has a profound effect on immune-system recognition. Because glycosylation is cell type specific, IgGs produced in different host cells contain different patterns of oligosaccharides, which could affect the biological functions. Even where cells, such as human embryonic stem cells, are grown on mouse feeder layers in the presence of animal-derived serum replacements, the cells incorporated a nonhuman, and immunogenic, sialic acid, and the sialic acid was then found on the cell surface. (Martin, M. J., et al., Nature Medicine, 2005, 11:228-232). Although the therapeutic antibody industry has tried to avoid these problems by producing less antigenic IgG with defucosylated oligosaccharides, defucosylated antibodies are not equivalent to humanized antibodies, and may still have immunogenecity issues, as well as having different half-lives than natural human antibodies.

Metabolic oligosaccharide engineering refers to the introduction of subtle modifications into monosaccharide residues within cellular glycans. Researchers have used metabolic engineering to disrupt glycan biosynthesis, chemically modify cell surfaces, probe metabolic flux inside cells, and to identify specific glycoprotein subtypes from the proteome. (reviewed in Dube, D. H., and Bertozzi, C. R., Current Opinion in Chemical Biology, 2003, 7:616-625).

There is a need for antibodies that have tags or labels at sites other than the binding region, and for antibodies that may be easily labeled using simple and efficient chemical reactions. There is also a need for antibodies that have post-translational modifications that are more like human antibodies.

SUMMARY OF THE INVENTION

The invention generally relates to methods of remodeling and labeling proteins and antibodies at novel oligosaccharide linkages, methods of humanizing antibodies by modifying glycosylation, as well as to antibodies or proteins linked to modified oligosaccharides. The antibodies or proteins, for example, IgGs, are labeled using either in vitro or in vivo methods.

In some in vitro embodiments, an oligosaccharide present on a first antibody is cleaved, and a different, second, oligosaccharide is attached to the cleavage site on the first antibody. This second oligosaccharide may be, for example, cleaved from a second antibody. Using this method, oligosaccharides obtained from, for example, human antibodies may be attached to antibodies generated in non-human cell lines. Also, using this method, secondary labels may be attached to the antibodies at an oligosaccharide.

In some in vivo embodiments, unnatural sugars having chemical handles are taken up by antibody-producing cells, and incorporated into the oligosaccharides on the antibodies. Once the antibodies are isolated, secondary labels may be attached at the chemical handles.

By labeling antibodies at glycan residues in the Fc portion of the antibody, instead of the traditional labeling of cysteine or lysine residues in the binding region of the antibody, possible disruption of epitope binding is avoided. In addition, the number of glycan residues present on the IgG, is generally known. In contrast, each epitope-specific IgG may have a different number of lysine or cysteine residues in the peptide sequence, and each may have a different ability to be labeled, based on the IgG structure. Therefore, it would generally be difficult to determine how many labels were present on each IgG. Using the methods of the present invention, it is expected that about all of the glycan residues are labeled, which allows for quantitative labeling and detection of the antibodies using, for example, fluorescence-activated cell sorting (FACS).

In other methods of the invention, the ligation of human oligosaccharides to non-human IgG would result in glycoforms practically identical to those in humans, with the only difference being an extra galactose near the sugar attachment point, and a ring structure from the cycloaddition.

Besides the humanization of therapeutic antibodies, there are many possible applications for the methods of the present invention. For example, glycosylation patterns can alter in certain diseases or conditions such as, for example, rheumatoid arthritis and pregnancy. The ability to mix and match oligosaccharides may enable researchers to investigate human diseases involving altered glycosylation in animal models.

One aspect of the invention provides a method of producing a glycomodified protein, comprising:
  attaching a modified sugar comprising a chemical handle to a GlcNAc residue on a first protein; and
  mixing said first protein with a reporter molecule, carrier molecule or solid support capable of reacting with said chemical handle;
  wherein said reporter molecule, carrier molecule or solid support attaches to the protein at said chemical handle, thereby forming a glycomodified protein.

In another embodiment, said first protein is an antibody. In a more particular embodiment, the antibody is IgG.

In another embodiment, the attaching step is in a solution substantially free of proteases.

In another embodiment, prior to the attaching step, the method comprises: cleaving an oligosaccharide present on a first protein at a GlcNAc-GlcNAc linkage to obtain a protein comprising a GlcNAc residue. In a more particular embodiment, said oligosaccharide is cleaved using endoglycosidase H cleavage at the GlcNAc-GlcNAc linkage. In another embodiment, said oligosaccharide is cleaved using endoglycosidase M cleavage at the GlcNAc-GlcNAc linkage.

In another embodiment, said reporter molecule, carrier molecule or solid support is attached to said GlcNAc using a mutant galactosyl transferase. In another embodiment, said mutant is a Y289L mutant.

In another embodiment, said modified sugar is an azide-modified sugar and said reporter molecule, carrier molecule or solid support is labeled with alkyne or activated alkyne. More particularly, said azide-modified sugar is UDP-GalNAz.

In another embodiment, prior to the attaching step, the method comprises:
cleaving an oligosaccharide present on a second protein at a GlcNAc-GlcNAc linkage to obtain an oligosaccharide having a GlcNAc residue;
binding said oligosaccharide to the reporter molecule, solid support or carrier molecule capable of reacting with said chemical handle.

In another embodiment, the oligosaccharide having a GlcNAc residue is treated with ammonium bicarbonate and said oligosaccharide is attached to an alkyne by a succinimidyl ester. In another embodiment, said second protein is synthesized in a different cell line or cell type than said first protein. In another embodiment, said second protein is synthesized in a human cell.

In another embodiment, the reporter molecule is selected from the group consisting of a fluorescent dye, an enzyme, a radiolabel, a metal chelator, or a detectable substrate. In another embodiment, the carrier molecule is selected from the group consisting of therapeutic agents, DNA, protein, peptides, and sugars.

In another embodiment, the glycomodified protein becomes more or less antigenic as compared to the first protein before it is modified. In another embodiment, the first protein is derived from a non-human source. In another embodiment, the glycomodified protein is humanized.

In another embodiment, said cleavage of said first protein is performed in the presence of an OH-alkyne, and said endoglycosidase M attaches said OH-alkyne to the cleaved GlcNAc residue; and said modified oligosaccharide is labeled with an azide residue.

Another aspect of the invention provides a method of labeling an protein by labeling an oligosaccharide attached to said protein, comprising incubating an protein-producing cell in the presence of an unnatural sugar, wherein said unnatural sugar comprises a chemical handle.

Another aspect of the invention provides an antibody comprising a labeled oligosaccharide.

Irrespective of their location, the embodiments are provided as more particular descriptions of any one of the aspects of the invention.

Other objects, features and advantages of the present invention will become apparent from the detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 15 depicts gels showing the results of separating proteins labeled using the click reaction with different chelators. The samples and click labeling conditions are the same as for FIG. 14, except that chelator treatments include addition of either 5 mM TPEN, BCS or Neocuproine at the beginning of the reaction. After labeling, the samples were precipitated, resolubilized in LDS buffer+5 mM TCEP and serial 2-fold dilutions were performed. Dilutions were loaded onto 4-12% BIS-TRIS gels with MOPS running buffer (250 ng each of ovalbumin and myglobin in lane 1).

DETAILED DESCRIPTION OF THE INVENTION

Figure 1:
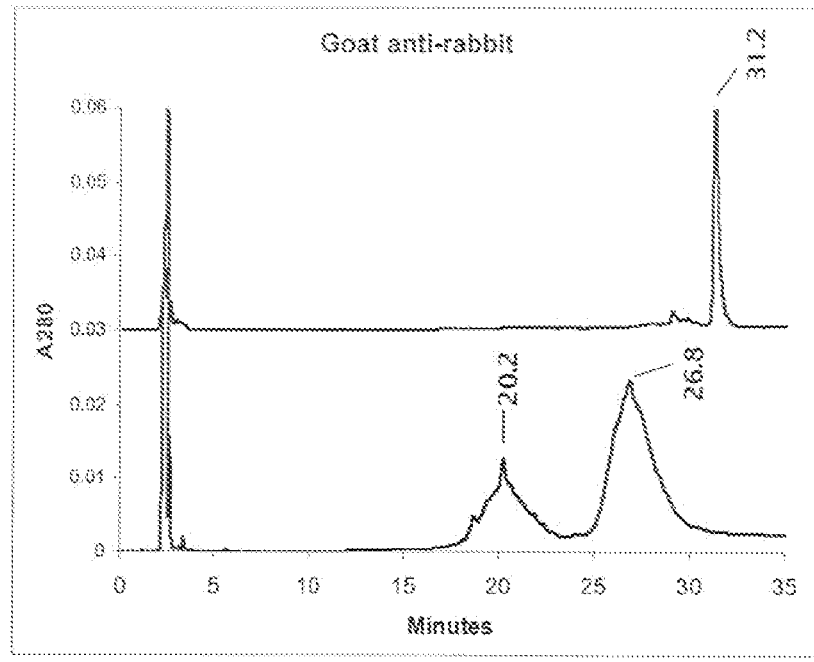
FIG. 1 shows a comparison of undigested (lower panel) and EndoH$_f$-treated (top panel) goat anti-rabbit polyclonal antibody by HPLC. For undigested antibody the light chain eluted at 20.2 minutes and the glycosylated heavy chain at 26.8 minutes. For EndoH$_f$-treated antibody, the fully deglycosylated heavy chain eluted at 31.2 minutes.

Introduction:

Various glycosidase enzymes, such as Endo-H are able to cleave N-linked oligosaccharides and other enzymes, such as Gal-T are able to transfer select oligoaccharides to an acceptor molecule containing an —OH group. The most efficient acceptor molecules are N-acetylglucosamine and glucose. Alternatively, select sugars can be introduced to an acceptor, such as a protein through metabolic labeling. The use of this enzyme or metabolic system in several applications that involve decoration of proteins with oligosaccharides (e.g. therapeutic antibodies) or the conjugation of proteins to solid substrates with oligosaccharides is described herein. Some applications may include the transfer of oligosaccharides to protein containing complementary chemical handles for solid support surfaces coated with appropriate acceptor molecules. Additionally, sugars could be transferred to a detection molecule such as a fluorescent or fluorogenic compound that would enhance detection, purification, and characterization or proteins by mass spectrometry. Transfer to a macromolecule containing an appropriate acceptor OH group plus an affinity peptide tag, reactive chemical moiety (e.g. azide, alkyne), or a biotin is also possible.

One preferred application of this methodology is the humanization of non-human antibodies by replacing the non-human N-linked oligosaccharides with human N-linked oligosaccharides derived from human antibodies. In this case, the non-human antibody is decorated with a set of heterogeneous human oligosaccharides. Alternatively, a homogenous purified or synthetic human-type oligosaccharide, attached to a protein or peptide substrate, could be used as a donor to impart specific properties to the antibody acceptor. Such properties might include the regulation of serum half-life, targeting to specific cell or tissues e.g. Fc receptors, or alteration of antibody stability. The donor could also contain a functional moiety such as a metal chelator, a fluorescent molecule, an antigen, an oligonucleotide, a biotin compound, or a cellular ligand.

Definitions:

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Unless defined otherwise, all technical and scientific terms used herein have the same meaning as commonly understood by one of ordinary skill in the art to which this invention is related. The following terms are defined for purposes of the invention as described herein.

TABLE 1

List of Abbreviations

| Abbreviation | Term. |
| --- | --- |
| GalNAz | N-alpha-azidoacetylgalactosamine. |
| GlcNAz | N-alpha-azidoacetylglucosamine. |
| GalNAc | N-acetylgalactosamine. |
| GlcNAc | N-acetylglucosamine |
| LOS | Lipooligosaccharide. |
| ManLev | N-levulinoylmannosamine. |
| ManNAc | N-acetylmannosamine. |
| ManNAz | N-alpha-azidoacetylmannosamine. |
| ManNBut | N-butanoylmannosamine. |
| ManNProp | N-propanoylmannosamine. |
| NCAM | neural cell adhesion molecule. |
| PSA | Polysialic acid. |
| Endo H | Endoglycosidase H |
| Endo M | Endoglycosidase M |

The term "acceptor" as used herein refers to a substituent capable of forming an endoglycosidase catalyzed bond with an oligosaccharide or monosaccharide comprising a donor. Preferably, the acceptor unit is a GlcNAc residue appended to an antibody. More preferably, the acceptor unit is a GlcNAc that is targeted by Endo-M or Endo-A and is bound to an additional saccharide moiety prior to contact with Endo-M or Endo-A.

The term "donor" as used herein refers to a substituent capable of forming an endoglycosidase catalyzed bond with an oligosaccharide or monosaccharide acceptor. Preferably, the donor unit is a GlcNAc residue appended to an asparagine. More preferably, the donor unit is a GlcNAc that is targeted Endo-M or Endo-A and is bound to an additional GlcNAc moiety prior to contact with Endo-M or Endo-A. Preferred donors comprise the structure: Asn-GlcNAc-X, wherein X is the oligosaccharide or monosaccharide that is transferred to the target protein comprising an acceptor.

The term "activated alkyne," as used herein, refers to a chemical moiety that selectively reacts with an alkyne modified group on another molecule to form a covalent chemical bond between the alkyne modified group and the alkyne reactive group. Examples of alkyne-reactive groups include azides. "Alkyne-reactive" can also refer to a molecule that contains a chemical moiety that selectively reacts with an alkyne group.

The term "affinity," as used herein, refers to the strength of the binding interaction of two molecules, such as an antibody and an antigen or a positively charged moiety and a negatively charged moiety. For bivalent molecules such as antibodies, affinity is typically defined as the binding strength of one binding domain for the antigen, e.g. one Fab fragment for the antigen. The binding strength of both binding domains together for the antigen is referred to as "avidity". As used herein "High affinity" refers to a ligand that binds to an antibody having an affinity constant ($K_a$) greater than $10^4$ $M^{-1}$, typically $10^5$-$10^{11}$ $M^{-1}$; as determined by inhibition ELISA or an equivalent affinity determined by comparable techniques such as, for example, Scatchard plots or using $K_d$/dissociation constant, which is the reciprocal of the $K_a$.

The term "alkyne reactive," as used herein, refers to a chemical moiety that selectively reacts with an alkyne modified group on another molecule to form a covalent chemical bond between the alkyne modified group and the alkyne reactive group. Examples of alkyne-reactive groups include azides. "Alkyne-reactive" can also refer to a molecule that contains a chemical moiety that selectively reacts with an alkyne group.

The term "antibody" as used herein refers to an immunoglobulin molecule or immunologically active portion thereof, i.e., an antigen-binding portion. Examples of immunologically active portions of immunoglobulin molecules include immunoglobulin molecules or fragments thereof that comprise the F(ab) region and a sufficient portion of the Fc region to comprise the oligosaccharide linkage site, for example, the asparagine-GlcNAc linkage site. An antibody sometimes is a polyclonal, monoclonal, recombinant (e.g., a chimeric or humanized), fully human, non-human (e.g., murine), or a single chain antibody. An antibody may have effector function and can fix complement, and is sometimes coupled to a toxin or imaging agent. An antibody is, for example, an IgG.

The term "antibody fragments" as used herein refers to fragments of antibodies that retain the principal selective binding characteristics of the whole antibody. Particular fragments are well-known in the art, for example, Fab, Fab', and F(ab')$_2$, which are obtained by digestion with various proteases, pepsin or papain, and which lack the Fc fragment of an intact antibody or the so-called "half-molecule" fragments obtained by reductive cleavage of the disulfide bonds connecting the heavy chain components in the intact antibody. Such fragments also include isolated fragments consisting of the light-chain-variable region, "Fv" fragments consisting of the variable regions of the heavy and light chains, and recombinant single chain polypeptide molecules in which light and heavy variable regions are connected by a peptide linker. Other examples of binding fragments include (i) the Fd fragment, consisting of the VH and CH 1 domains; (ii) the dAb fragment (Ward, et al., Nature 341, 544 (1989)), which consists of a VH domain; (iii) isolated CDR regions; and (iv) single-chain Fv molecules (scFv) described above. In addition, arbitrary fragments can be made using recombinant technology that retains antigen-recognition characteristics.

The term "antigen" as used herein refers to a molecule that induces, or is capable of inducing, the formation of an antibody or to which an antibody binds selectively, including but not limited to a biological material. Antigen also refers to "immunogen". The target-binding antibodies selectively bind an antigen, as such the term can be used herein interchangeably with the term "target".

The term "anti-region antibody" as used herein refers to an antibody that was produced by immunizing an animal with a select region that is a fragment of a foreign antibody wherein only the fragment is used as the immunogen. Regions of antibodies include the Fc region, hinge region, Fab region, etc. Anti-region antibodies include monoclonal and polyclonal antibodies. The term "anti-region fragment" as used herein refers to a monovalent fragment that was generated from an anti-region antibody of the present invention by enzymatic cleavage.

The term "aqueous solution" as used herein refers to a solution that is predominantly water and retains the solution characteristics of water. Where the aqueous solution contains solvents in addition to water, water is typically the predominant solvent.

The term "azide reactive" as used herein refers to a chemical moiety that selectively reacts with an azido modified group on another molecule to form a covalent chemical bond between the azido modified group and the azide reactive group. Examples of azide-reactive groups include alkynes and phospines (e.g. triaryl phosphine). "Azide-reactive" can also refer to a molecule that contains a chemical moiety that selectively reacts with an azido group.

The term "buffer" as used herein refers to a system that acts to minimize the change in acidity or basicity of the solution against addition or depletion of chemical substances.

The term "carrier molecule" as used herein refers to a biological or a non-biological component that is covalently bonded to compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term, "chemical handle" as used herein refers to a specific functional group, such as an azide, alkyne, activated alkyne, phosphite, phosphine, and the like. The chemical handel is distinct from the reactive group, defined below, in that the chemical handle are moieties that are rarely found in naturally-occurring biomolecules and are chemically inert towards biomolecules (e.g, native cellular components), but when reacted with an azide- or alkyne-reactive group the reaction can take place efficiently under biologically relevant conditions (e.g., cell culture conditions, such as in the absence of excess heat or harsh reactants).

The term "click chemistry," as used herein, refers to the Huisgen cycloaddition or the 1,3- dipolar cycloaddition between an azide and a terminal alkyne to form a 1,2,4-triazole. Such chemical reactions can use, but are not limited to, simple heteroatomic organic reactants and are reliable, selective, stereospecific, and exothermic.

The term "cycloaddition" as used herein refers to a chemical reaction in which two or more $\pi$-electron systems (e.g., unsaturated molecules or unsaturated parts of the same molecule) combine to form a cyclic product in which there is a net reduction of the bond multiplicity. In a cycloaddition, the $\pi$ electrons are used to form new $\pi$ bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 1,3-dipolar cycloadditions, occur between a 1,3-dipole and a dipolarophile and are typically used for the construction of five-membered heterocyclic rings. The terms "[3+2] cycloaddition" also encompasses "copperless" [3+2] cycloadditions between azides and cyclooctynes and difluorocyclooctynes described by Bertozzi et al. J. Am. Chem. Soc., 2004, 126: 15046-15047.

The term "detectable response" as used herein refers to an occurrence of, or a change in, a signal that is directly or indirectly detectable either by observation or by instrumentation. Typically, the detectable response is an occurrence of a signal wherein the fluorophore is inherently fluorescent and does not produce a change in signal upon binding to a metal ion or biological compound. Alternatively, the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction, and electron density.

The term "detectably distinct" as used herein refers to a signal that is distinguishable or separable by a physical property either by observation or by instrumentation. For example, a fluorophore is readily distinguishable either by spectral characteristics or by fluorescence intensity, lifetime, polarization or photo-bleaching rate from another fluorophore in the sample, as well as from additional materials that are optionally present.

The term "directly detectable" as used herein refers to the presence of a material or the signal generated from the material is immediately detectable by observation, instrumentation, or film without requiring chemical modifications or additional substances.

The term "fluorophore" as used herein refers to a composition that is inherently fluorescent or demonstrates a change in fluorescence upon binding to a biological compound or metal ion, i.e., fluorogenic. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, September 2002).

The term "glycomodified" refers to a particle such as a protein or antibody that is altered to change the number or configuration of sugar molecules attached thereto. A preferred glycomodified antibody is a non-human derived therapeutic antibody that becomes humanized based on the alteration of its sugar appendages.

The term "glycoprotein" as used herein refers to a protein that has been naturally glycosolated and those that have been enzymatically modified, in vivo or in vitro, to comprise a sugar group.

The term "humanized" as used herein refers to modification of a protein, such as an antibody, such that it is less immunogenic or invokes a reduced immune response in a human as compared to the non-humanized counterpart. Preferably, non-human proteins and antibodies are humanized by modification of sugar groups to be more similar or identical to those expressed in humans.

The term "kit" as used herein refers to a packaged set of related components, typically one or more compounds or compositions.

The term "label," as used herein, refers to a chemical moiety or protein that is directly or indirectly detectable (e.g. due to its spectral properties, conformation or activity) when attached to a target or compound and used in the present methods, including reporter molecules, solid supports and carrier molecules. As used herein, label as collectively refers to a reporter molecule, solid support or carrier molecule. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidase (HRP) to bind to the tag, and then use a calorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their calorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS ($10^{th}$ edition, CD-ROM, September 2005), supra.

The term "linker" or "L", as used herein, refers to a single covalent bond or a series of stable covalent bonds incorporating 1-30 nonhydrogen atoms selected from the group consisting of C, N, O, S and P. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a reporter molecule, carrier molecule or solid support, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol., 124: 913-920 (1980); Bouizar et al., Eur. J. Biochem., 155: 141-147 (1986); Park et al., J. Biol. Chem., 261: 205-210 (1986); Browning et al., J. Immunol., 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The terms "protein" and "polypeptide" are used herein in a generic sense to include polymers of amino acid residues of any length. The term "peptide" is used herein to refer to polypeptides having less than 100 amino acid residues, typically less than 10 amino acid residues. The terms apply to amino acid polymers in which one or more amino acid residues are an artificial chemical analogue of a corresponding naturally occurring amino acid, as well as to naturally occurring amino acid polymers.

The term "purified" as used herein refers to a preparation of a glycoprotein that is essentially free from contaminating proteins that normally would be present in association with the glycoprotein, e.g., in a cellular mixture or milieu in which the protein or complex is found endogenously such as serum proteins or cellular lysate.

The term "reactive group" as used herein refers to a group that is capable of reacting with another chemical group to form a covalent bond, i.e. is covalently reactive under suitable reaction conditions, and generally represents a point of attachment for another substance. As used herein, reactive groups refer to chemical moieties generally found in biological systems and that react under normal biological conditions, these are herein distinguished from the azido and activated alkyne moieties of the present invention. The reactive group is a moiety, such as carboxylic acid or succinimidyl ester, that is capable of chemically reacting with a functional group on a different compound to form a covalent linkage. Reactive groups generally include nucleophiles, electrophiles and photoactivatable groups.

The term "reporter molecule" refers to any moiety capable of being attached to a modified post translationally modified protein of the present invention, and detected either directly or indirectly. Reporter molecules include, without limitation, a chromophore, a fluorophore, a fluorescent protein, a phosphorescent dye, a tandem dye, a particle, a hapten, an enzyme and a radioisotope. Preferred reporter molecules include fluorophores, fluorescent proteins, haptens, and enzymes.

The term "sample" as used herein refers to any material that may contain an analyte of interest or a modified post translationally modified protein of the present invention. The analyte may include a reactive group, e.g., a group through which a compound of the invention can be conjugated to the analyte. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

The term "solid support," as used herein, refers to a material that is substantially insoluble in a selected solvent system, or which can be readily separated (e.g., by precipitation) from a selected solvent system in which it is soluble. The term solid support includes semi-solid supports. Solid supports useful in practicing the present invention can include groups that are activated or capable of activation to allow selected species to be bound to the solid support. Solid supports may be present in a variety of forms, including a chip, wafer or well, onto which an individual, or more than one compound, of the invention is bound such as a polymeric bead or particle.

The term "Staudinger ligation" as used herein refers to a chemical reaction developed by Saxon and Bertozzi (E. Saxon and C. Bertozzi, Science, 2000, 287: 2007-2010) that is a modification of the classical Staudinger reaction. The classical Staudinger reaction is a chemical reaction in which the combination of an azide with a phosphine or phosphite produces an aza-ylide intermediate, which upon hydrolysis yields a phosphine oxide and an amine. A Staudinger reaction is a mild method of reducing an azide to an amine; and triphenylphosphine is commonly used as the reducing agent. In a Staudinger ligation, an electrophilic trap (usually a methyl ester) is appropriately placed on a triarylphosphine (usually in ortho to the phosphorus atom) and reacted with the azide, to yield an aza-ylide intermediate, which rearranges in aqueous media to produce a compound with amide group and a phosphine oxide function. The Staudinger ligation is so named because it ligates (attaches/covalently links) the two starting molecules together, whereas in the classical Staudinger reaction, the two products are not covalently linked after hydrolysis.

The terms "structural integrity of the [biomolecule] is not reduced" or "preservation of the structural integrity of the

[biomolecule]", as used herein, means that either: 1) when analyzed by gel electrophoresis and detection (such as staining), a band or spot arising from the labeled biomolecule is not reduced in intensity by more than 20%, and preferably not reduced by more than 10%, with respect to the corresponding band or spot arising from the same amount of the electrophoresed unlabeled biomolecule, arising from the labeled biomolecule analyzed; or 2) when analyzed by gel electrophoresis, a band or spot arising from the labeled biomolecule is not observed to be significantly less sharp than the corresponding band or spot arising from the same amount of the electrophoresed unlabeled biomolecule, where "significantly less sharp" (synonymous with "significantly more diffuse") means the detectable band or spot takes up at least 5% more, preferably 10% more, more preferably 20% more area on the gel than the corresponding unlabeled biomolecule. Other reproducible tests for structural integrity of labeled biomolecules include, without limitation detection of released amino acids or peptides, or mass spectrometry.

By an antibody being "synthesized" in a cell is meant that the antibody is either naturally produced in, and isolated from, said cell, or that the antibody is synthesized using recombinant methods in said cell and is then isolated.

The term "about" as used herein refers to a value sometimes within 10% of the underlying parameter (i.e., plus or minus 10%), a value sometimes within 5% of the underlying parameter (i.e., plus or minus 5%), a value sometimes within 2.5% of the underlying parameter (i.e., plus or minus 2.5%), or a value sometimes within 1% of the underlying parameter (i.e., plus or minus 1%), and sometimes refers to the parameter with no variation. Thus, a distance of "about 20 nucleotides in length" includes a distance of 19 or 21 nucleotides in length (i.e., within a 5% variation) or a distance of 20 nucleotides in length (i.e., no variation) in some embodiments. As used herein, the article "a" or "an" can refer to one or more of the elements it precedes (e.g., a protein microarray "a" protein may comprise one protein sequence or multiple proteins). The term "or" is not meant to be exclusive to one or the terms it designates. For example, as it is used in a phrase of the structure "A or B" may denote A alone, B alone, or both A and B In general, for ease of understanding the present invention, the metabolic and enzymatic labeling of biomolecules with azide moieties, alkyne moieties or phosphine, and the chemical labeling of such moieties with azide reactive moieties, alkyne reactive moieties or phosphine reactive moieties will first be described in detail. This will be followed by some embodiments in which such labeled biomolecules can be detected, isolated and/or analyzed. Exemplified methods are then disclosed.

Methods of the Invention

Preparation of Antibodies and Antibody-producing Cells

Antibodies for use in cleavage and substitution of oligosaccharides of the present invention may be produced using any means known to those of ordinary skill in the art. General information regarding procedures for antibody production and labeling may be found, for example, in Antibodies: A Laboratory Manual, Cold Spring Harbor Laboratory, Chap. 14 (1988). Cell lines expressing antibodies for in vivo metabolic labeling may also be produced using any means known to those of ordinary skill in the art. For therapeutic purposes, chimeric, humanized, and completely human antibodies are useful for applications that include repeated administration to subjects. Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al International Application No. PCT/US86/02269; Akira, et al European Patent Application 184,187; Taniguchi, M., European Patent Application 171,496; Morrison et al European Patent Application 173,494; Neuberger et al PCT International Publication No. WO 86/01533; Cabilly et al U.S. Pat. No. 4,816,567; Cabilly et al European Patent Application 125,023; Better et al., Science 240: 1041-1043 (1988); Liu et al., Proc. Natl. Acad. Sci. USA 84: 3439-3443 (1987); Liu et al., J. Immunol 139: 3521-3526 (1987); Sun et al., Proc. Natl. Acad. Sci. USA 84: 214-218 (1987); Nishimura et al., Canc. Res. 47: 999-1005 (1987); Wood et al., Nature 314: 446-449 (1985); and Shaw et al., J. Natl. Cancer Inst. 80: 1553-1559 (1988); Morrison, S. L., Science 229: 1202-1207 (1985); Oi et al., BioTechniques 4: 214 (1986); Winter U.S. Pat. No. 5,225,539; Jones et al., Nature 321: 552-525 (1986); Verhoeyan et al., Science 239: 1534; and Beidler et al., J. Immunol. 141: 4053-4060 (1988).

Transgenic mice that are incapable of expressing endogenous immunoglobulin heavy and light chains genes, but that can express human heavy and light chain genes, may be used to produce human antibodies for use in the present invention. See, for example, Lonberg and Huszar, Int. Rev. Immunol. 13: 65-93 (1995); and U.S. Pat. Nos. 5,625,126; 5,633,425; 5,569,825; 5,661,016; and 5,545,806. In addition, companies such as Invitrogen (Carlsbad, Calif.), Abgenix, Inc. (Fremont, Calif.), and Medarex, Inc. (Princeton, N.J.), can be engaged to provide human antibodies directed against a selected antigen using technology similar to that described above. Human antibodies that recognize a selected epitope also can be generated using a technique referred to as "guided selection." In this approach a selected non-human monoclonal antibody (e.g., a murine antibody) is used to guide the selection of a completely human antibody recognizing the same epitope. This technology is described for example by Jespers et al., Bio/Technology 12: 899-903 (1994).

Glycoproteins:

The glycoprotein constituent of this invention may be any glycoprotein, including for example, hormones, enzymes, antibodies, viral receptors, viral surface glycoproteins, parasite glycoproteins, parasite receptors, T-cell receptors, MHC molecules, immune modifiers, tumor antigens, mucins, inhibitors, growth factors, trophic factors, lymphokines, cytokines, toxoids, nerve growth hormones, blood clotting factors, adhesion molecules, multidrug resistance proteins, adenylate cyclases, bone morphogenic proteins and lectins.

Also included among the glycoproteins are the hormones and cytokines. Examples of hormones include follicle stimulating hormone, human chorionic gonadotropin, luteinizing hormone, thyrotrophin and ovine, bovine, porcine, murine and rat alleles of these hormones. Examples of cytokine glycoproteins include .alpha.-interferon, lymphotoxin, and interleukin-2. Also included are glycoprotein tumor-associated antigens, for example, carcinoembryonic antigen (CEA), human mucins, her-2/neu, and prostate-specific antigen (PSA) [R. A. Henderson and O. J. Finn, Advances in Immunology, 62, pp. 217-56 (1996)].

Alternatively, the glycoprotein constituent may be selected from personal care glycoproteins, including cosmetic glycoproteins, veterinary glycoproteins, food glycoproteins, feed glycoproteins, diagnostic glycoproteins, glycoproteins used in chemical reactions, glycoproteins used in industrial methods, cleaning agent glycoproteins, including detergent glycoproteins, and decontamination glycoproteins. Included among such glycoproteins are enzymes, such as, for example, hydrolases, transferases, isomerases, lyases, ligases, transferases and oxidoreductases. Examples of hydrolases include lipase, cholinesterase, alkaline phosphatase, .beta.-amylase deoxyribonuclease, glucoamylase A and B, .alpha.-galactosidase I and II, .beta.-fructofuranosidase, .beta.-glucouronidaDse, N-acetyl-.beta.-glucosaminidase, hyaluronidase, oxytocinase, kallikrein, bromelain, enterokinase, proteinase a, b, and c, pepsinogen and pepsin. Examples of oxidoreductases include glucose oxidase, peroxidase and chloroperoxidase. Examples of transferases include .gamma.-glutamyl-transpeptidase and ribonuclease.

Additional glycoproteins contemplated for use in the present invention include cross-linked glycoproteins, such as those described in U.S. Pat. No. 6,359,118, the contents of which are incorporated by reference.

In Vitro Modification of IgG Oligosaccharides

Oligosaccharides are attached to asparagine residues on immunoglobulin gamma (IgG) antibodies by an N-acetylglucosamine disaccharaide linkage (GlcNac-GlcNac). In general, each IgG has two sites near the neck of the IgG where oligosaccharides are attached by GlcNac-GlcNac linkages. Treatment with an endoglycosidase, such as, for example, Endoglycosidase H (Endo H) cleaves between the two GlcNac sugars. The cleaved end of each sugar is referred to as the "reducing end." By cleaving the oligosaccharide from a first IgG, and collecting the cleaved oligosaccharide, an oligosaccharide having a reducing-end GlcNAc is obtained. A second IgG is then treated with an endoglycosidase, such as, for example, EndoH. This second IgG, which has a GlcNAc having a reducing end is then collected. The reducing end of the GlcNAc residue attached to the first oligosaccharide, and the reducing end of the GlcNAc residue oligosaccharide attached to the second IgG may then be treated so that the first oligosaccharide may be attached to the second IgG.

One method of attaching the first oligosaccharide is, for example, by chemically conjugating the first oligosaccharide to an alkyne. For example, the reducing end may be converted to an amine by treatment with ammonium bicarbonate, then the alkyne may be attached via a succinimidyl ester. An azide-modified sugar, such as UDP-GalNAz is then attached to the reducing end of the GlcNAc residue on the second IgG. This transfer may occur, for example, using a mutant galactosyl transferase. The azide-labeled IgG is then mixed with the alkyne-labeled oligosaccharide. The alkyne and azide moieties undergo a cycloaddition reaction, which ligates the oligosaccharide from the first IgG to the oligosaccharide on the second IgG.

Removal of Oligosaccharides from IgG

Oligosaccharides are attached to IgG at asparagine residues on the Fc Portion of the antibody (FIG. 1B). At the amino acid, there are two GlcNAc sugars attached to each other by a beta (1-4) linkage. The enzyme Endo-H cleaves this linkage, so that one GlcNAc residue remains attached to the asparagine on the IgG, while the other GlcNac remains attached to the rest of the oligosaccharide. The GlcNAc attached to the oligosaccharide contains a reactive reducing-end, which can be selectively modified without altering the other sugar residues.

Attaching an Azide to the IgG GlcNAc

The enzyme galactosyl transferase normally transfers a galactose from UDP-galactose to a terminal GlcNAc residue. Khidekel et al (J. Am. Chem. Soc. 2003, 125:16162-16163; Hsieh-Wilson, L., et al., U.S. Patent Publication No. 20050130235, published Jun. 16, 2005, U.S. Ser. No. 10/990, 767) used a mutant enzyme, a Y289L mutant, to transfer an acetone-containing galactose substrate to a GlcNAc residue. An azide-containing galactose substrate (UDP-GalNAz) may be synthesized for transfer to the GlcNAc site by the mutant galactosyl transferase.

Attaching an Alkyne to the Reducing-end of the Cleaved Oligosaccharide

The reducing-end of a sugar is a reactive site that can be selectively modified. Some saccharides do not containing reducing ends (such as sucrose), rendering them more stable than saccharides with exposed reducing-ends. When the enzyme Endo-H cleaves the GlcNAc-GlcNAc linkage, the reducing end of the oligosaccharide GlcNAc is exposed.

Using the method of Tamura et al. (Analytical Biochem. 1994, 216:335-344), the reducing ends of N-linked oligosaccharides may be converted into amines by reaction with ammonium bicarbonate, resulting in an oligosaccharide-glycosylamine. This reaction may be conducted using methods known to those of skill in the art, and may, for example, be conducted using a 10-ml glass screw top vial, with about 10 micromoles of oligosaccharide in the presence of about 1 gram of ammonium bicarbonate in about 0.5 ml water, and heating the mixture at about 50° C. for about 24 hours. The resulting oligosaccharide-glycosylamines may be reacted with, for example, acylating agents in order to attach fluorophores, or an N-glycyl linker which itself may be capable of accepting other biological or biophysical probes.

For example, a tyrosine may be attached to the amine with a Boc-protected tyrosine succinimidl ester. The Boc protection helps to avoid polymerization of a tyrosine succinimidyl ester. An alkyne-succinimidyl ester is then obtained and may be used in a conjugation scheme. Where a tyrosine residue is attached, the oligosaccharide may be quantified using $A280_{nm}$.

Labeling of Glycoproteins Using [3+2] Cycloaddition

Azides and terminal alkynes undergo a cycloaddition reaction in the presence of a copper catalyst. This cycloaddition reaction may be conducted using the methods of, for example, Sharpless et al. (U.S. Patent Application Publication No. 20050222427, published Oct. 6, 2005, PCT /US03/17311; Lewis W G, et al., Angewandte Chemie-Int'l Ed. 41 (6): 1053; method reviewed in Kolb, H. C., et al., Angew. Chem. Inst. Ed. 2001, 40:2004-2021), which developed reagents that react with each other in high yield and with few side reactions in a heteroatom linkage (as opposed to carbon-carbon bonds) in order to create libraries of chemical compounds. The reaction is conducted in the presence of a metal catalyst and a reducing agent. For example, Cu(II) may be included in the reaction, in the presence of a reducing agent such as, but not limited to, ascorbate, metallic copper, quinone, hydroquinone, vitamin $K_1$, glutathione, cysteine, $Fe^{2+}$, $Co^{2+}$, and an applied electric potential. Further preferred reducing agents include metals selected from the group consisting of Al, Be, Co, Cr, Fe, Mg, Mn, Ni, and Zn. Other metals that may catalyze this type of cycloaddition reaction include, for example, Au, Ag, Hg, Cd, Zr, Ru, Fe, Co, Pt, Pd, Ni, Rh, and W. Those of ordinary skill in the art would be able to determine the appropriate metal to use for the intended ligand.

In Vitro Modification of IgG Using EndoM or Endo A

EndoM (or Endo A) are endoglycosidases with glycosyltransferase activities. The enzymes cleaves the disaccharide GlcNAc-GlcNAc between the two residues, as does EndoH. EndoM has an additional enzymatic activity in that once an oligosaccharide having the GlcNAc residue is cleaved, the enzyme will attach the reducing end of the GlcNAc residue to an OH group. Thus, in other methods of the invention, is provided an in vitro method of labeling a cleaved oligosaccharide with an alkyne. In one example, an IgG comprising an oligosaccharide having a GlcNAc-GlcNAc linkage is incubated in the presence of EndoM as well as an OH-alkyne.

One aspect of the invention provides a method of producing a glycomodified antibody comprising at least one monosaccharide or oligosaccharide, the method comprising:

contacting an antibody with Endo-M or Endo-A and a donor comprising the monosaccharide or oligosaccharide to form a contacted solution, wherein the antibody comprises an acceptor;

incubating the contacted solution for a sufficient amount of time for a covalent bond to form between the acceptor and the monosaccharide or oligosaccharide; and obtaining the glycomodified antibody.

In a more particular embodiment, the antibody is derived from a non-human source. More particular still, the antibody is derived from murine cells, plant cells, goat cells, rabbit cells, yeast cells, or CHO cells. In another embodiment, the glycomodified antibody is humanized.

In another embodiment, the acceptor is N-acetylglucosamine (GlcNAc), wherein the GlcNAc. In another embodiment, the antibody is contacted with Endo-M. In another embodiment, the antibody is contacted with Endo-A. In another embodiment, the donor comprises: Asn-GlcNAc-X, wherein X is the oligosaccharide or monosaccharide. More particularly, X is -GlcNAc-(oligosaccharide or monosaccharide).

In another embodiment, the monosaccharide or oligosaccharide comprise an alkynyl or azido functionality. In another embodiment, the monosaccharide or oligosaccharide comprise a chemical handle.

In another embodiment, the monosaccharide or oligosaccharide comprise a reporter molecule. More particularly, the reporter molecule is a fluorescent dye, an enzyme, a radiolabel, a metal chelator, or a detectable substrate.

In another embodiment, the monosaccharide or oligosaccharide comprise a carrier molecule, a solid support, a receptor, a ligand, a peptide, a protein, a nucleic acid polymer, a polysaccharide, an antigen, or a hapten.

In another embodiment, the obtaining step comprises purifying the glycomodified antibody. More particularly, subsequent to purifying, the glycomodified antibody is combined with an excipient, diluent or pharmaceutically acceptable salt. More particular still, the glycomodified antibody combined with an excipient, diluent or pharmaceutically acceptable salt, is administered to a patient in need thereof.

In another embodiment, the glycomodified antibody is a therapeutic antibody. More particularly, the therapeutic antibody is selected from the group consisting of trastuzumab, cetuximab, bevacizumab, alemtuzumab, gemtuzumab, ibritumomab, rituximab, and panitumumab.

In another embodiment, the monosaccharide or oligosaccharide affects the serum half life of the glycomodified antibody, targets the glycomodified antibody to a particular cell or tissue, or affects the stability of the glycomodified antibody.

In another embodiment, the contacting step is performed in an aqueous solution. In another embodiment, the contacting step is performed in an organic solution. In another embodiment, the contacting step is performed in a protic solution. In another embodiment, the contacting step is performed in a polar solution. In another embodiment, the contacting step is performed in a solvent that is not a ketone or furan.

In another embodiment, the glycomodified antibody comprises at least one oligosaccharide.

In another embodiment, the antibody is a monoclonal antibody. In another embodiment, the antibody is a polyconal antibody.

Another aspect of the invention provides a method of covalently bonding a monosaccharide or oligosaccharide to an antibody, the method comprising:

contacting the antibody with Endo-M or Endo-A and a donor comprising the monosaccharide or oligosaccharide to form a contacted solution, wherein the antibody comprises an acceptor; and incubating the contacted solution for a sufficient amount of time for a covalent bond to form between the acceptor and the monosaccharide or oligosaccharide.

Another aspect of the invention provides a method of humanizing a therapeutic antibody, the method comprising:

contacting the therapeutic antibody with Endo-M or Endo-A and a donor comprising a monosaccharide or oligosaccharide to form a contacted solution, wherein the antibody comprises an acceptor; and incubating the contacted solution for a sufficient amount of time for a covalent bond to form between the acceptor and the monosaccharide or oligosaccharide, thereby forming a humanized therapeutic antibody.

In another embodiment, the therapeutic antibody is a monoclonal antibody.

In another embodiment, the therapeutic antibody is selected from the group consisting of trastuzumab, cetuximab, bevacizumab, alemtuzumab, gemtuzumab, ibritumomab, rituximab, and panitumumab.

Another aspect of the invention provides a kit for forming a detectable glycomodified antibody comprising:

(a) Endo-M or Endo-A;
(b) a donor comprising an oligosaccharide or monosaccharide; and
(c) instructions for forming the detectable glycomodified antibody.

In another embodiment, the oligosaccharide or monosaccharide comprises a reporter group, an azide group, or an alkynyl group.

In another embodiment, the reporter molecule is a fluorescent dye, enzyme, radiolabel, a metal chelator, or a detectable substrate.

Another aspect of the invention provides a composition comprising:

(a) an antibody comprising an acceptor;
(b) Endo-M or Endo-A;
(c) a donor comprising an oligosaccharide or monosaccharide; and
(d) a solvent.

Metabolic Labeling of Antibodies in Antibody-producing Cells

In vivo metabolic labeling methods may be used to label antibodies in antibody-producing cells such as, for example, hybridoma cells, and any other cell that produces antibodies or recombinant antibodies. Antibody-producing cells may be fed unnatural sugar substrates, for example unnatural sugar substrates that contain a reactive chemical/affinity handle. The chemical handles may be, for example, but not limited to, azides, triarylphosphines, or alkyne residues that may, for example, participate in "click" chemistry type reactions. In certain embodiments, the unnatural sugars comprise modifications that are small enough to be incorporated into the cells. The cellular metabolic machinery incorporates the substrates into N- or O-linked glycans attached to the antibodies. Once the in vivo labeled antibodies are released and isolated from the cells, the labeled antibodies may be directly labeled using a detection/affinity/immobilization compound that is reactive with the chemical handles. These compounds may include, for example, but are not limited to, fluorophores, solid support resins, microarray slides, or affinity tags.

Metabolic Labeling of Antibodies

Antibody-producing cells are incubated in the presence of unnatural sugars, for example, using the methods of Bertozzi et al., U.S. Pat. No. 6,936,701, which provides examples of incubating cells in the presence of unnatural sugars to modify cell-surface glycoproteins. The cells may be incubated with, for example, about 20 mM of the unnatural sugar for, for example, about 72 hours.

Synthesis of Unnatural Sugar Substrates

Unnatural sugar substrates may be synthesized that incorporate reactive chemical handles that may be used for click chemistry. The azide/alkyne cycloaddition reaction can be used to introduce affinity probes (biotin), dyes, polymers (e.g., poly(ethylene glycol) or polydextran) or other monosaccharides (e.g., glucose, galactose, fucose, O-GlcNAc, mannose-derived saccharides bearing the appropriate chemical handle). In certain embodiments, these handles include, for example, azide, triarylphosphine, or alkyne residues. The chemical handle also can be an azido group capable of reacting in a Staudinger reaction (see, for example, Saxon, E,.et al., J. Am. Chem. Soc., 2002,124(50): 14893-14902). The Staudinger reaction involves reaction between trivalent phosphorous compounds and organic azides (Staudinger et al., Helv. Chim. Acta 1919, 2:635), has been used for a multitude of applications. (Gololobov et al. Tetrahedron 1980, 37, 437); (Gololobov et al. Tetrahedron 1992, 48, 1353). The phosphine can have a neighboring acyl group such as an ester, thioester or N-acyl imidazole (i.e. a phosphinoester, phosphinothioester, phosphinoimidazole) to trap the aza-ylide intermediate and form a stable amide bond upon hydrolysis. The phosphine can also be typically a di- or triarylphosphine to stabilize the phosphine.

Unnatural sugar substrates that may be incorporated in vivo according to the present invention include, for example, but are not limited to, GalNAz, ManNaz, and GlcNAz. Unnatural sugar substrates include, for example, sugar substrates that comprise small sugar groups that the cellular machinery would be more likely to incorporate, and not recognize as being foreign.

Labeling Cleaved Oligosaccharides and in Vivo Labeled IgGs

Various labels, or tags, (reporter molecule, solid support and carrier molecule) may be linked or conjugated to the cleaved oligosaccharide for the in vitro methods of the present invention, which would then be attached to the cleaved IgGs of the methods of the present invention. These labels or tags may also be used to label or tag the in vivo-sugar modified IgGs isolated from the cells after metabolic labeling; the labels or tags may be attached at the chemical/affinity handles on the unnatural sugars incorporated during metabolic labeling.

The labels or tags may be, for example, a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, melphalan, carmustine (BCNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Antibody conjugates can be used for modifying a given biological response. For example, the drug moiety may be DNA or a protein or polypeptide possessing a desired biological activity. Such proteins may include, for example, a toxin such as abrin, ricin A, pseudomonas exotoxin, or diphtheria toxin; a polypeptide such as tumor necrosis factor, gamma.-interferon, .alpha.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Also, an antibody can be conjugated to a second antibody to form an antibody heteroconjugate as described by Segal in U.S. Pat. No. 4,676,980, for example.

The labels or tags may also, for example, be detectable labels used, for example, for diagnostic or research purposes, or tags used for binding of the antibody to other biomolecules or reagents (such as, for example, biotin/avidin binding, or binding of the antibody to microarray chips, beads, or plates). Examples of such labels or tags include, but are not limited to fluorescent dyes, such as, for example, fluorescein (FITC), Oregon Green 488 dye, Marina Blue dye, Pacific Blue dye, and Texas Red-X dye, Alexa Fluor dyes (Invitrogen, Carlsbad, Calif.); compounds containing radioisotopes; light-scattering compounds such as, for example, those containing gold or silver; dyes; light producing compounds such as, for example, luciferase; haptens, such as, for example, biotin, desthiobiotin, DSB-X biotin, and dinitrophenol (DNP); enzymes, such as, for example, horseradish peroxidase (HRP), alkaline phosphatase, and [beta]-lactamase; phycobiliproteins, such as, for example, R-phycoerythrin (R-PE, allophycocyanin (AP); and particles, such as, for example, Qdots, gold, ferrofluids, dextrans and microspheres.

Reporter Molecules:

The reporter molecules of the present invention include any directly or indirectly detectable reporter molecule known by one skilled in the art that can be attached to a modified glycoprotein of the present invention. Reporter molecules include, without limitation, a chromophore, a fluorophore, a fluorescent protein, a phosphorescent dye, a tandem dye, a particle, a hapten, an enzyme and a radioisotope. Preferred reporter molecules include fluorophores, fluorescent proteins, haptens, and enzymes.

A fluorophore of the present invention is any chemical moiety that exhibits an absorption maximum beyond 280 nm, and when covalently attached to a labeling reagent retains its spectral properties. Fluorophores of the present invention include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1, 3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S.; Pat. Nos. 4,981,977; 5,268,486; 5,569,587; 5,569,766; 5,486, 616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyril, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof As used herein, oxazines include resorufins (including any corresponding compounds disclosed in U.S. Pat. No. 5,242,805), aminooxazinones, diaminooxazines, and their benzo-substituted analogs.

When the fluorophore is a xanthene, the fluorophore is optionally a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276; 5,846,737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Preferred fluorophores of the invention include xanthene (rhodol, rhodamine, fluorescein and derivatives thereof) coumarin, cyanine, pyrene, oxazine and borapolyazaindacene. Most preferred are sulfonated xanthenes, fluorinated xanthenes, sulfonated coumarins, fluorinated coumarins and sulfonated cyanines. The choice of the fluorophore attached to the labeling reagent will determine the absorption and fluorescence emission properties of the labeling reagent and immuno-labeled complex. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

In one aspect of the invention, the fluorophore has an absorption maximum beyond 480 nm. In a particularly useful embodiment, the fluorophore absorbs at or near 488 nm to 514 nm (particularly suitable for excitation by the output of the argon-ion laser excitation source) or near 546 nm (particularly suitable for excitation by a mercury arc lamp).

Many of fluorophores can also function as chromophores and thus the described fluorophores are also preferred chromophores of the present invention.

In addition to fluorophores, enzymes also find use as labels for the detection reagents. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. However, fluorophores are most preferred because they do not require additional assay steps and thus reduce the overall time required to complete an assay. The enzyme substrate is selected to yield the preferred measurable product, e.g. colorimetric, fluorescent or chemiluminescence. Such substrates are extensively used in the art, many of which are described in the MOLECULAR PROBES HANDBOOK, supra.

A preferred colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other calorimetric oxidoreductase substrates that yield detectable products include, but are not limited to: 2,2-azino-bis (3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042), Amplex UltraRed and its variants in (WO05042504) and reduced dihydroxanthenes, including dihydrofluoresceins (U.S. Pat. No. 6,162,931) and dihydrorhodamines including dihydrorhodamine 123. Peroxidase substrates that are tyramides (U.S. Pat. Nos. 5,196,306; 5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Another preferred calorimetric (and in some cases fluorogenic) substrate and enzyme combination uses a phosphatase enzyme such as an acid phosphatase, an alkaline phosphatase or a recombinant version of such a phosphatase in combination with a calorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986).

Glycosidases, in particular beta-galactosidase, beta-glucuronidase and beta-glucosidase, are additional suitable enzymes. Appropriate calorimetric substrates include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. Preferred fluorogenic substrates include resorufin beta-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl beta-D-galactopyranoside, carboxyumbelliferyl beta-D-galactopyranoside and fluorinated coumarin beta-D-galactopyranosides (U.S. Pat. No. 5,830,912).

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In addition to enzymes, haptens such as biotin are also preferred labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

Fluorescent proteins also find use as labels for the labeling reagents of the present invention. Examples of fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of a target in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorophore then emits at a wavelength farther from the fluorescent proteins than could have been obtained with only the fluorescent protein. A particularly useful combination is the phycobiliproteins disclosed in U.S. Pat. Nos. 4,520,110; 4,859,582; 5,055,556 and the sulforhodamine fluorophores disclosed in U.S. Pat. No. 5,798,276, or the sulfonated cyanine fluorophores disclosed in U.S. Ser. Nos. 09/968/401 and 09/969/853; or the sulfonated xanthene derivatives disclosed in U.S. Pat. No. 6,130,101 and those combinations disclosed in U.S. Pat. No. 4,542,104. Alternatively, the fluorophore functions as the energy donor and the fluorescent protein is the energy acceptor.

In an exemplary embodiment is provided glycoproteins covalently conjugated to a carrier molecule. This includes, but is not limited to, any azide modified glycoprotein and any carrier molecule disclosed herein.

Provided in one embodiment is a first composition that comprises a present glycoprotein, a first reporter molecule, and a carrier molecule. Provided in another embodiment is a second glycoprotein that includes a first composition in combination with a second conjugate. The second conjugate comprises a carrier molecule or solid support, as disclosed below, that is covalently bonded to a second reporter molecule. The first and second reporter molecules have different structures and preferably have different emission spectra. Even more preferably, the first and second reporter molecules are selected so that their fluorescence emissions essentially do not overlap. In another embodiment the reporter molecules have different excitation spectra, alternatively the reporter molecules are excited by the same laser.

Carrier Molecules:

The carrier molecule (or solid support) of the conjugates in the second composition may be the same or a different molecule. The discussion herein pertaining to the identity of various carrier molecules is generally applicable to this embodiment of the invention as well as other embodiments.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an IgG binding protein, a fluorescent protein, agarose, and a non-biological microparticle.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCO$alkyl and combinations thereof Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis OR), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds of the present invention function as a reporter molecule for the specific binding pair. Exemplary binding pairs are set forth in Table 2.

TABLE 2

Representative Specific Binding Pairs

| antigen | antibody |
|---|---|
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization In a particular aspect the carrier molecule is an antibody fragment, such as, but not limited to, anti-Fc, an anti-Fc isotype, anti-J chain, anti-kappa light chain, anti-lambda light chain, or a single-chain fragment variable protein; or a non-antibody peptide or protein, such as, for example but not limited to, soluble Fc receptor, protein G, protein A, protein L, lectins, or a fragment thereof. In one aspect the carrier molecule is a Fab fragment specific to the Fc portion of the target-binding antibody or to an isotype of the Fc portion of the target-binding antibody (U.S. Ser. No. 10/118,204). The monovalent Fab fragments are typically produced from either murine monoclonal antibodies or polyclonal antibodies generated in a variety of animals, for example but not limited to, rabbit or goat. These fragments can be generated from any isotype such as murine IgM, $IgG_1$, $IgG_{2a}$, $IgG_{2b}$ or $IgG_3$.

Alternatively, a non-antibody protein or peptide such as protein G, or other suitable proteins, can be used alone or coupled with albumin. Preferred albumins include human and bovine serum albumins or ovalbumin. Protein A, G and L are defined to include those proteins known to one skilled in the art or derivatives thereof that comprise at least one binding domain for IgG, i.e. proteins that have affinity for IgG. These proteins can be modified but do not need to be and are conjugated to a reactive label in the same manner as the other carrier molecules of the invention.

In another aspect the carrier molecule is a whole intact antibody. Antibody is a term of the art denoting the soluble substance or molecule secreted or produced by an animal in response to an antigen, and which has the particular property of combining specifically with the antigen that induced its formation. Antibodies themselves also serve are antigens or immunogens because they are glycoproteins and therefore are used to generate anti-species antibodies. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds).

When IgG is treated with the enzyme papain a monovalent antigen-binding fragment can be isolated, referred herein to as a Fab fragment. When IgG is treated with pepsin (another proteolytic enzyme), a larger fragment is produced, $F(ab')_2$. This fragment can be split in half by treating with a mild reducing buffer that results in the monovalent Fab' fragment.

The Fab' fragment is slightly larger than the Fab and contains one or more free sulfhydryls from the hinge region (which are not found in the smaller Fab fragment). The term "antibody fragment" is used herein to define the Fab', F(ab')$_2$ and Fab portions of the antibody. It is well known in the art to treat antibody molecules with pepsin and papain in order to produce antibody fragments (Gorevic et al., Methods of Enzyol., 116:3 (1985)).

The monovalent Fab fragments of the present invention are produced from either murine monoclonal antibodies or polyclonal antibodies generated in a variety of animals that have been immunized with a foreign antibody or fragment thereof, U.S. Pat. No. 4,196,265 discloses a method of producing monoclonal antibodies. Typically, secondary antibodies are derived from a polyclonal antibody that has been produced in a rabbit or goat but any animal known to one skilled in the art to produce polyclonal antibodies can be used to generate anti-species antibodies. The term "primary antibody" describes an antibody that binds directly to the antigen as opposed to a "secondary antibody" that binds to a region of the primary antibody. Monoclonal antibodies are equal, and in some cases, preferred over polyclonal antibodies provided that the ligand-binding antibody is compatible with the monoclonal antibodies that are typically produced from murine hybridoma cell lines using methods well known to one skilled in the art.

In one aspect the antibodies are generated against only the Fc region of a foreign antibody. Essentially, the animal is immunized with only the Fc region fragment of a foreign antibody, such as murine. The polyclonal antibodies are collected from subsequent bleeds, digested with an enzyme, pepsin or papain, to produce monovalent fragments. The fragments are then affinity purified on a column comprising whole immunoglobulin protein that the animal was immunized against or just the Fc fragments.

In an exemplary embodiment is provided azido glycoproteins covalently conjugated to a solid support. This includes, but is not limited to, any azido glycoprotein disclosed above and any solid support disclosed herein.

Provided in one embodiment is a first composition that comprises a present compound, a first reporter molecule, and a solid support. Provided in another embodiment is a second composition that includes a first composition in combination with a second conjugate. The second conjugate comprises a solid support or carrier molecule, as disclosed above, that is covalently bonded to a second reporter molecule. The first and second reporter molecules have different structures and preferably have different emission spectra. Even more preferably, the first and second reporter molecules are selected so that their fluorescence emissions essentially do not overlap. In another embodiment the reporter molecule have different excitation spectra, alternatively the reporter molecules are excited by the same laser.

The solid support (or carrier molecule) of the conjugates in the second composition may be the same or a different molecule. The discussion herein pertaining to the identity of various solid supports is generally applicable to this embodiment of the invention as well as other embodiments.

Solid Supports:

A variety of solid supports are useful in the present invention. A solid support suitable for use in the present invention is typically substantially insoluble in liquid phases and contains a substituent capable of reacting with a chemical handle. In a preferred embodiment, the solid supports comprise an alkyne or activated alkyne and react with an azide on a modified sugar, or vice versa. Solid supports of the current invention are not limited to a specific type of support and include semi-solid supports. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Kits:

Kits are provided that comprise components for in vivo metabolic labeling of proteins and antibodies. Such kits may comprise, for example, unnatural sugars labeled with a chemical/affinity handle, such as, for example, azides, triarylphosphines, or alkynes. Such kits may further comprise, for example, reagents for labeling or tagging metabolically labeled antibodies isolated from cells. For example, a kit may comprise an unnatural oligosaccharide, such as, for example, GalNAz, ManNAz, or GlcNAz. The kit may further comprise a fluorophore label, or an affinity tag, that is reactive with the chemical/affinity handle on the unnatural oligosaccharide. Those of ordinary skill in the art are aware of the various labels or tags that may be used to label or tag the modified antibodies, for example, but not limited to, those listed herein. For example, the label or tag may be linked to an alkyne, that is capable of a click chemistry-type reaction once contacted with the azide on the metabolically-labeled antibody.

The kits of the present invention may also comprise one or more of the components in any number of separate containers, packets, tubes, vials, microtiter plates and the like, or the components may be combined in various combinations in such containers. For the kits of the present invention, for example, the unnatural oligosaccharide, comprising the chemical/affinity handle may be provided in a separate container than the fluorophore label or affinity tag.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Particular Aspects of the Invention:

The methods of the present invention can be used for directly labeling the terminal saccharide residue on a glycoprotein or antibody, such as with the Gal-T enzyme described herein. Alternatively, a saccharide group is cleaved, such as with Endo-H, and then a saccharide comprising the chemical handle is added to the protein or antibody, such as with Endo-M or Endo-A (both of which are capable of cleavage and transfer of the sugar). In another embodiment, a saccharide comprising a chemical handle is introduced to a glycoprotein or antibody through metabolic labeling. Reference to "saccharide" indicates monosaccharide or oligosaccharide.

One aspect of the invention provides a method of producing a glycomodified protein, comprising
    cleaving an oligosaccharide present on a first protein at a GlcNAc-GlcNAc linkage to obtain a protein comprising a GlcNAc residue having a reducing end;
    attaching a modified sugar comprising a chemical handle to the reducing end of said GlcNAc residue; and
    mixing said first protein with a modified oligosaccharide having a label capable of reacting with said chemical handle;
    wherein said modified oligosaccharide attaches to the protein at said chemical handle, thereby forming a glycomodified protein.

In another embodiment, said protein is an antibody. More particularly, the antibody is an IgG. In another embodiment, said oligosaccharide is cleaved using endoglycosidase H cleavage at the GlcNAc-GlcNAc linkage. In another embodiment, said modified sugar is attached to said reducing end using a mutant galactosyl transferase. In another embodiment, said mutant is a Y289L mutant. In another embodiment, said modified sugar is an azide-modified sugar and said modified oligosaccharide is labeled with alkyne. In another embodiment, said azide-modified sugar is UDP-GalNAz.

In another embodiment, said modified oligosaccharide is obtained by
    cleaving an oligosaccharide present on a second protein at a GlcNAc-GlcNAc linkage to obtain an oligosaccharide having a GlcNAc residue having a reducing end;
    labeling said oligosaccharide with a label capable of reacting with said chemical handle.

In another embodiment, the reducing end of said cleaved oligosaccharide is treated with ammonium bicarbonate and said treated oligosaccharide is attached to an alkyne by a succinimidyl ester. In another embodiment, said second protein is synthesized in a different cell line or cell type than said first protein. In another embodiment, said second protein is synthesized in a human cell.

In another embodiment, said modified oligosaccharide further comprises a second label. In another embodiment, said second label is selected from the group consisting of therapeutic moieties, therapeutic agents, radioactive metal ions, DNA, protein, peptides, sugars, detectable labels, biotin, and avidin.

Another aspect of the invention provides oligosaccharide-modified protein obtained using the methods of any one of the embodiments.

Another aspect of the invention provides oligosaccharide-cleaved protein, obtained using the method comprising treating a protein with endoglycosidase H. In another embodiment, said protein is an antibody. More particularly, said antibody is an IgG.

Another aspect of the invention provides an antibody comprising a labeled oligosaccharide. In another embodiment, said label is selected from the group consisting of therapeutic moieties, therapeutic agents, radioactive metal ions, DNA, protein, peptides, sugars, detectable labels, biotin, and avidin.

In another embodiment, the oligosaccharide is cleaved using endoglycosidase M cleavage at the GlcNAc-GlcNAc linkage.

In another embodiment,
    said cleavage of said first antibody is performed in the presence of an OH-alkyne, and said endoglycosidase M attaches said OH-alkyne to the reducing end of said cleaved GlcNAc residue; and
    said modified oligosaccharide is labeled with an azide residue.

In another embodiment, said oligosaccharide is cleaved from said second antibody using endoglycosidase M cleavage at the GlcNAc-GlcNAc linkage.

In another embodiment,
    said cleavage of said second antibody is performed in the presence of an OH-alkyne, and said endoglycosidase M attaches said OH-alkyne to the reducing end of said cleaved GlcNAc residue, providing an alkyne-modified oligosaccharide; and
    said chemical handle on said modified sugar on said first antibody is an azide.

Another aspect of the invention provides an oligosaccharide-cleaved antibody, obtained using the method comprising treating an antibody with endoglycosidase M. In another embodiment, said antibody is an IgG.

Another aspect of the invention provides a method of labeling an antibody by labeling an oligosaccharide attached to said antibody, comprising incubating an antibody-producing cell in the presence of an unnatural sugar, wherein said unnatural sugar comprises a chemical handle.

In another embodiment, the antibody-producing cell is a recombinant cell. In another embodiment, said antibody-producing cell is a hybridoma. In another embodiment, said antibody is a IgG. In another embodiment, said chemical handle is selected from the group consisting of azides, triarylphosphines, or alkynes. In another embodiment, said unnatural sugar is selected from the group consisting of GalNAz, ManNaz, and GlcNAz.

Another embodiment further compres isolating said labeled antibody from said antibody-producing cell.

Another embodiment, further comprises attaching a second label to said isolated antibody, comprising contacting said isolated antibody with a second label that is reactive with said chemical handle.

In another embodiment, said chemical handle is an azide and said second label comprises or is modified to comprise an alkyne. In another embodiment, said second label is selected from the group consisting of therapeutic moieties, therapeutic agents, radioactive metal ions, DNA, protein, peptides, sugars, detectable labels, biotin, and avidin.

Another aspect of the invention provides labeled antibody obtained using the methods of any of embodiments described herein.

Another aspect of the invention provides a kit, comprising
    An unnatural sugar labeled with a chemical handle, and
    A secondary label that will attach to said unnatural sugar at said chemical handle.

In another embodiment, the kit further comprises instructions for in vivo labeling of antibodies in antibody-producing cells. In another embodiment, said chemical handle is selected from the group consisting of azides, triarylphosphines, and alkynes. In another embodiment, said unnatural sugar is selected from the group consisting of GalNAz, ManNAz, and GlcNAz. In another embodiment, said chemical handle is an azide and said secondary label comprises an alkyne.

The following examples describe specific aspects of the invention to illustrate the invention and to provide a description of the methods for those of skill in the art. The examples should not be construed as limiting the invention, as the examples merely provide specific methodology useful in understanding and practicing the invention. The reagents employed in the examples are commercially available or can be prepared using commercially available instrumentation, methods, or reagents known in the art. The foregoing examples illustrate various aspects of the invention and practice of the methods of the invention. Each of the references cited in the examples is incorporated herein by reference in its entirety. The examples are not intended to provide an exhaustive description of the many different embodiments of the invention nor to limit the selection of suitable reagents beyond what has already been described above. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

EXAMPLES

Example 1

Figure 2:
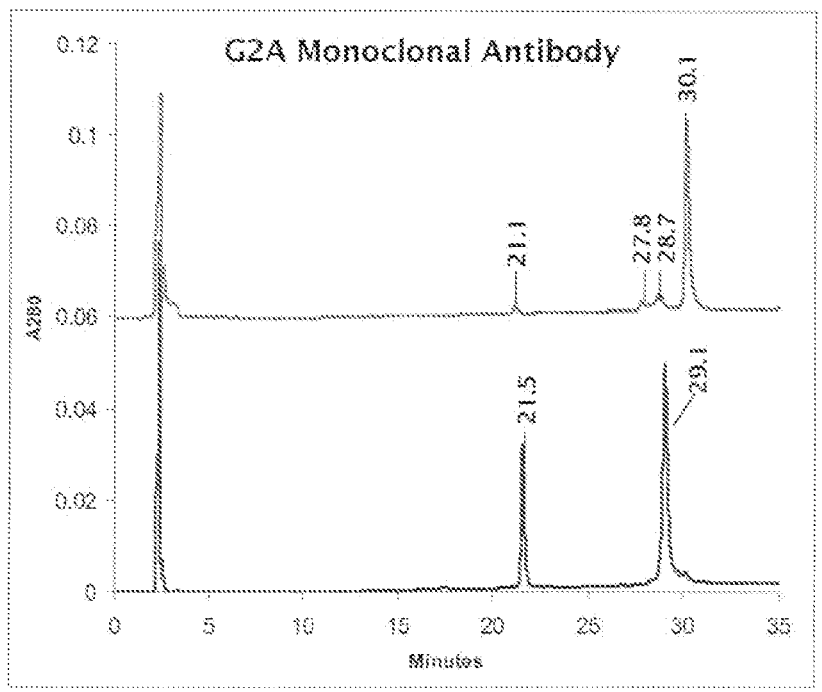
FIG. 2 shows a comparison of undigested (lower panel) and EndoH$_f$-treated (top panel) G2A monoclonal antibody analyzed by HPLC. For undigested antibody the light chain eluted at 21.5 minutes and glycosylated heavy chain at 29.1 minutes. For EndoH$_f$-treated antibody, the light chain eluted at 21.1 minutes, glycosylated or partially deglycosylated heavy chain at 27.8 and 28.7 minutes, and fully deglycosylated heavy chain at 30.1 minutes.

HPLC Verification of Monoclonal and Polyclonal Antibodies with and without Oligosaccharide Cleavage by Endo H Glycosidase Deglycosylation reaction: To 90 µL reduced and alkylated antibody (1 mg/ml) add 40 µL 0.5 M sodium citrate pH 5.5 and 10 µL EndoH$_f$ (1,000,000 U/mL, New England BioLabs). Incubate for 48 hours at 37° C. with rocking. Samples were centrifuged to remove precipitate and then injected directly onto the HPLC. Reversed-phase HPLC was performed on an Agilent Zorbax 300SB-CN column (4.6×150 mm, 3.5 µm) at 75° C. with a flow rate of 0.8 mL/min using a Waters 600E LC system. The mobile phase included water with 0.1% TFA in solvent A and 80% n-propanol, 10% acetonitrile, 10% water with 0.1% TFA in solvent B (conditons of Rehder et al., J. Chrom. A, 1102 (2006) 164-175). Separation was accomplished using a linear gradient from 20 to 40% B over 30 min. Results are depicted in FIG. 1 and FIG. 2.

Example 2

Figure 3A:
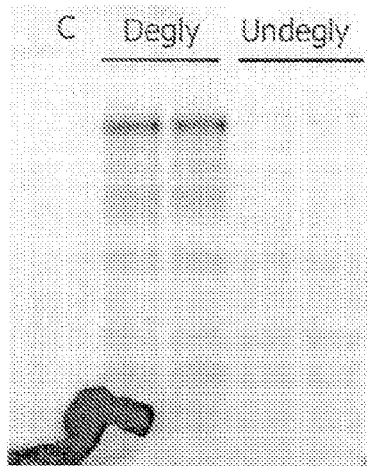
FIG. 3A shows TAMRA Click-iT™ label, showing labeling of chicken anti-goat heavy chain in Endo H-treated IgG (Degly), but not untreated IgG (Undegly). C: Control chicken anti-goat IgG starting material; Degly: Chicken anti-goat IgG after Endo H digestion, O-GlcNAc enzymatic labeling and Click iT detection; Undegly: Chicken anti-goat IgG after O-GlcNAc enzymatic labeling and Click iT detection.
Figure 3B:
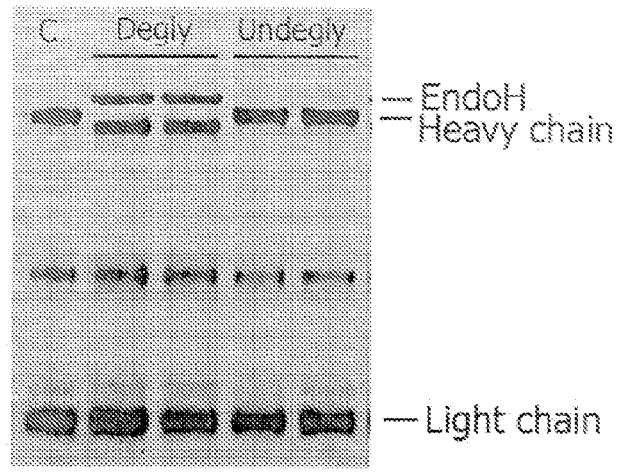
FIG. 3B shows the same gel described in FIG. 3A post-stained with SYPRO Ruby gel stain to show total protein pattern.

Enzymatic Labeling of Chicken Anti-goat Antibody with and without Oligosaccharide Cleavage by Endo H Glycosidase Chicken anti-goat IgG was washed into 50 mM MES pH 6.5 buffer on a VivaSpin 5000 MWCO filter column. For the deglycosylation reaction, an aliquot of washed IgG at 1 mg/mL was incubated 24 hours at 37° C. in 50 mM MES pH 6.5 containing 47.5 U/µL Endo H (New England BioLabs). Washed (undeglycosylated) or EndoH$_f$ digested IgG was then azido-labeled with the Click-iT O-GlcNAc enzymatic labeling kit using nondenaturing conditions: 0.5 mg/ml IgG in 50 mM MES pH 6.5, 120 mM NaCl, 11 mM MnCl$_2$, 0.1 mM ZnCl$_2$, 50 µM UDP-GalNAz, 5 U/mL Antarctic phosphatase, and 0.65 mg/mL GalT enzyme, overnight incubation at 4° C. The samples were purified through P10 sizing resin packed into a 0.5 mL spin column into 50 mM Tris pH 8. Collected fractions containing antibody were then labeled with the TAMRA Click-iT™ detection kit (C33370) and purified again through P10 sizing resin packed into a 0.5 mL spin column into 50 mM Tris pH 8 buffer. Approximately 250 ng was analyzed on a 4-12% BIS-TRIS gel using MOPS buffer. The gels were imaged on the BioRad FX imager using the 532 nm laser and 555 nm long pass emission filter (FIG. 3A). The gels were post-stained with SYPRO® Ruby protein gel stain and imaged using the 488 nm laser and 555 nm long pass emission filter (FIG. 3B).

Example 3

Metabolic Labeling of Antibodies with Azido Sugars

Figure 4A:
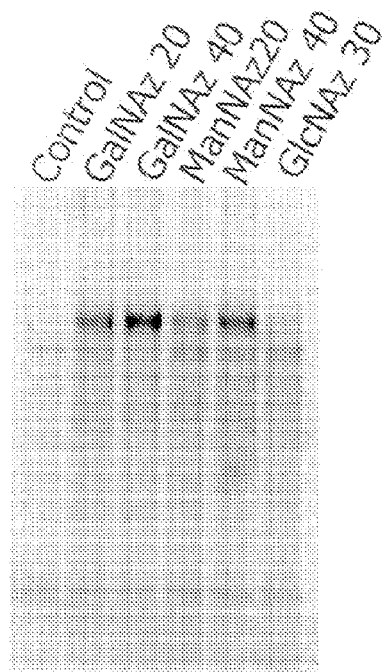
FIG. 4A shows M96 cells fed DMSO vehicle (control), or 20 μM Ac$_4$GalNAz, 40 μM Ac$_4$GalNAz, 20 μM Ac$_4$ManNAz, 40 μM Ac$_4$ManNAz, or 30 μM Ac$_4$GlcNAz, respectively, followed by Click iT detection of incorporated azido sugars.
Figure 4B:
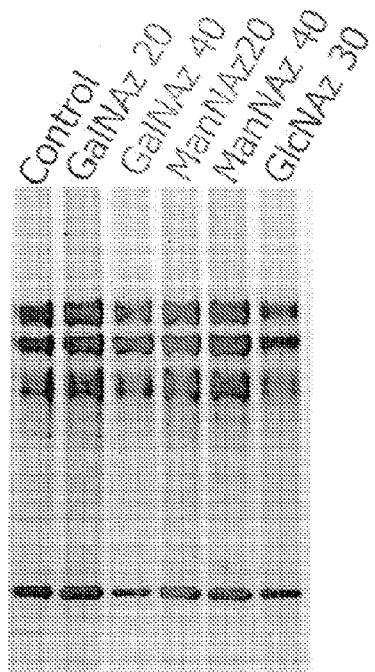
FIG. 4B shows the same gel described in FIG. 4A post-stained with SYPRO Ruby gel stain to show total protein pattern.

Mouse M96 hybridoma cells were fed the azido sugar analogues, Ac$_4$GalNAz, Ac$_4$ManNAz or Ac$_4$GlcNAz for five days. The cell supernatant (containing the azido-labeled monoclonal antibody) was collected and proteins were precipitated in chloroform/methanol. Precipitated pellets were resolubilized with 50 µL of 1% SDS, 100 mM TRIS pH 8, labeled with the TAMRA Click-iT™ detection kit (C33370) and 1 µg was analyzed on a 4-12% BIS-TRIS gel using MOPS buffer. The gels were imaged on the BioRad FX imager using the 532 nm laser and 555 nm long pass emission filter (FIG. 4A). The gels were post-stained with SYPRO® Ruby protein gel stain and imaged using the 488 nm laser and 555 nm long pass emission filter (FIG. 4B).

Example 4

Metabolic Labeling and "Click" Detection of Glycoprotein Subclasses

Figure 5A:
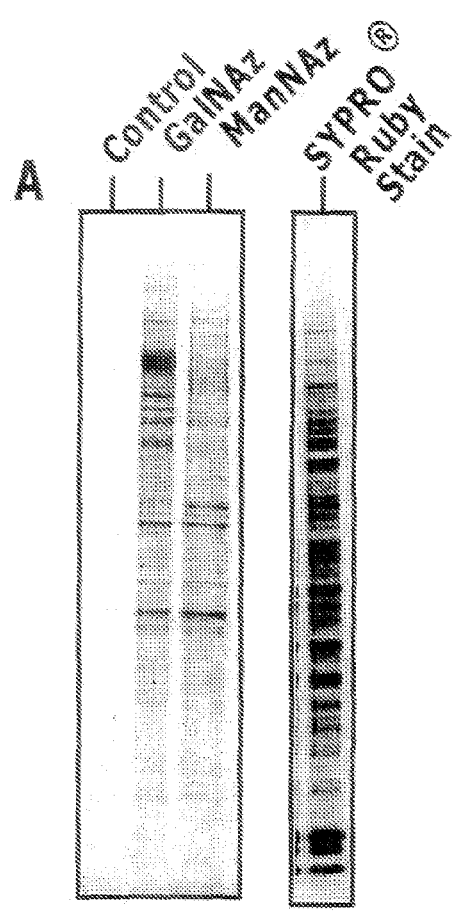
FIG. 5 shows metabolic labeling and "click" detection of glycoprotein subclasses A) and B) detection after separation on a gel and C schematically.
Figure 5B:
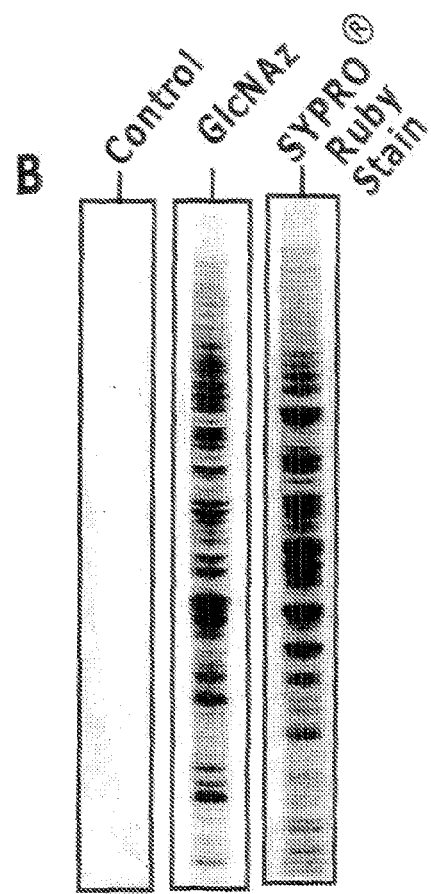
Figure 5C:
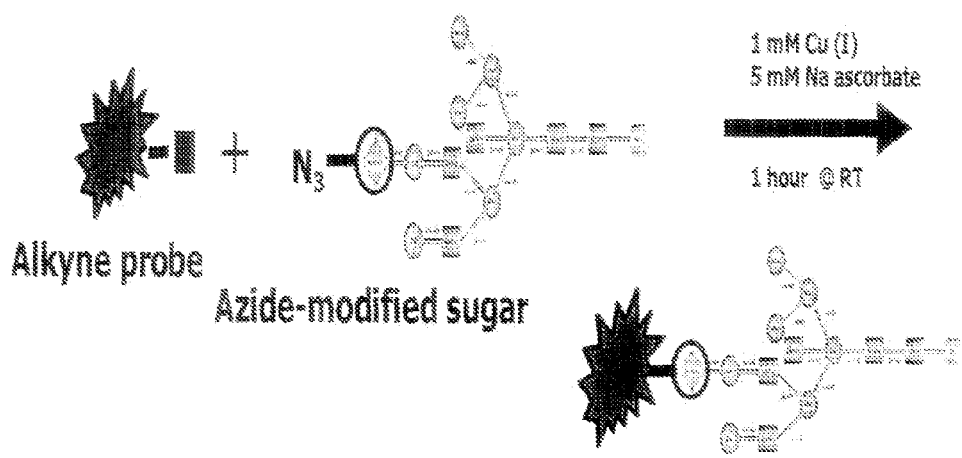

Jurkat cells were fed 40 µM Ac$_4$ManNAz or Ac$_4$GalNAz for 3 days (A) or 250 µM Ac$_4$GlcNAz overnight (B). Harvested cells were sonicated in 50 mM Tris buffer, pH 8.0 with protease and phosphatase inhibitors, and the lysates were subjected to high-speed centrifugation (100K×g). The membrane pellet proteins from ManNAz- and GalNAz-treated cells, and the soluble supernatant cells from the GlcNAc-treated cells, were precipitated with chloroform/methanol, dissolved in detergent, and labeled with a fluorescent alkyne probe in the presence of 1 mM CuSO4, and 5 mM ascorbic acid (1). 10 µg of the labeled, precipitated proteins were run on 1-D NuPAGE® Novex® 4-12% gels (Invitrogen). Images were obtained on the Fuji FLA-3000 scanner (Fuji) using 532 nm excitation (FIG. 5A). Gels were then post stained with SYPRO® Ruby stain (Invitrogen) and imaged using excitation at 473 nm (FIG. 5B). Control lanes represent extracts from unfed cells but treated with the fluorescent probe. See FIG. 5.

Example 5

Separation of Ac$_4$GlcNAz-treated Soluble Jurkat Cell Proteins by 2-D Gels

Figure 6:
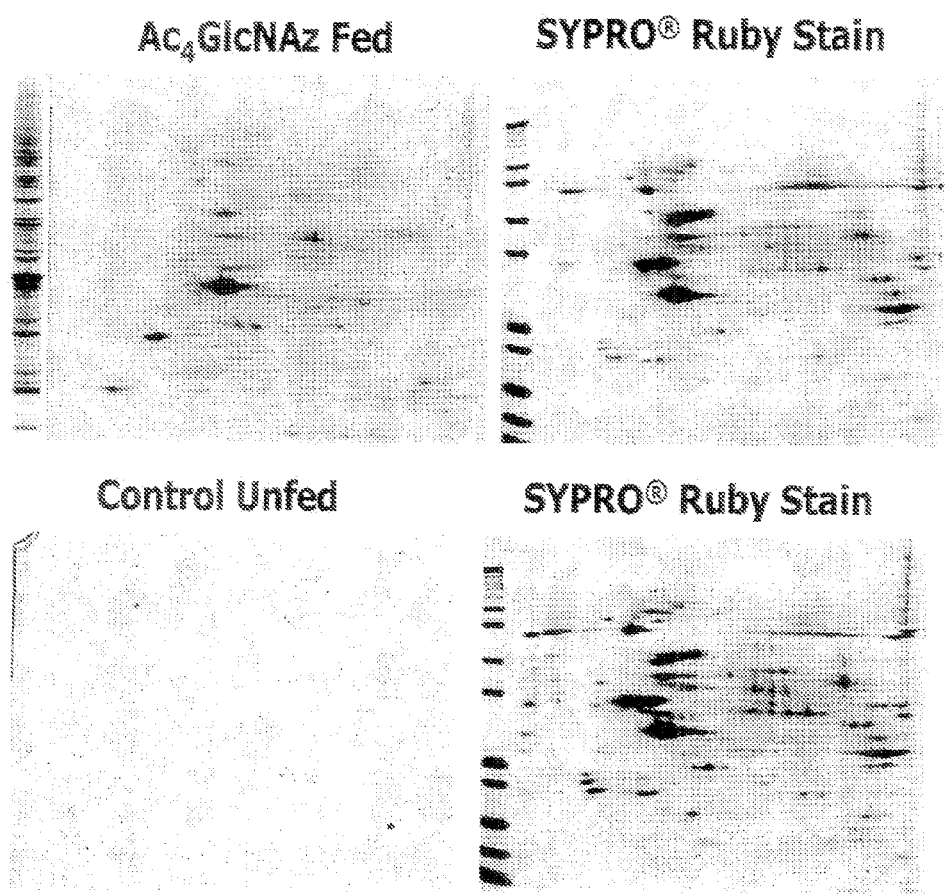
FIG. 6 shows soluble Jurkat cell proteins that had been fed Ac$_4$GlcNAz or DMSO vehicle (control unfed)—followed by Click iT detection of incorporated azido sugars and separation by 2-D polyacrylamide gel electrophoresis. The same gels were post-stained with SYPRO Ruby gel stain to show total protein pattern.

Jurkat cells were cultured overnight with 250 µM Ac$_4$GlcNAz or DMSO vehicle (control unfed). Soluble lysate proteins were prepared as for Example 4 using sonication and ultracentrifugation and labeled for 1 hour with a fluorescent alkyne probe. 40 µg of the labeled proteins were precipitated and resolubilized in 7 M urea, 2 M thiourea, 65 mM DTT, 2% CHAPS, 1% Zwittergent 3-10, 1% pH 3-10 carrier ampholytes and separated on pH 3-10 IEF strips in the first dimension and 4-12% Bis-Tris gels with MOPS buffer in the second dimension. Images were obtained on the Fuji FLA-3000 scanner (Fuji) using 532 nm excitation Gels were then post stained with SYPRO® Ruby stain (Invitrogen) and imaged again using excitation at 473 nm. See FIG. 6.

Example 6

Figure 7:
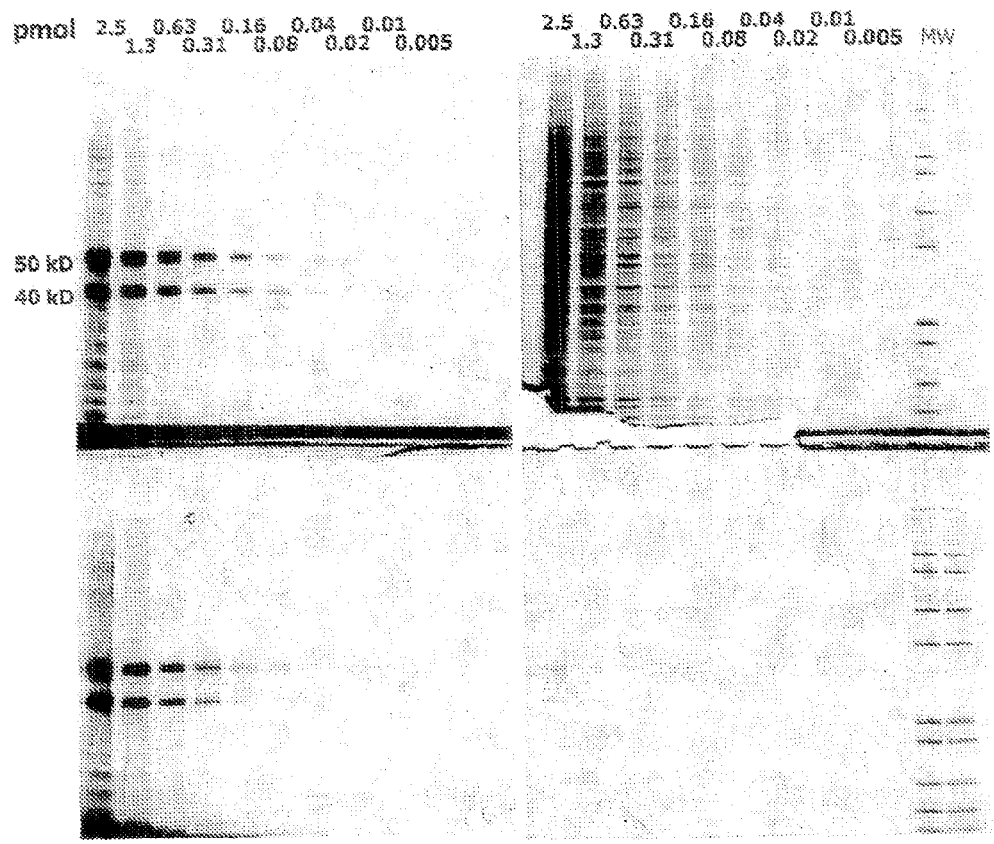
FIG. 7 shows in gel detection of 40 and 50 kD azide-labeled model proteins, which were first labeled with a fluorescent alkyne tag and then separated on the gel.

In Gel Detection of 40 and 50 kD azide-labeled Model Proteins 25 pmols each of 40 and 50 kD model proteins with single N-terminal azides were spiked into 100 µg of Jurkat cell lysates (upper panels), or not (lower panels). Proteins were labeled with a fluorescent alkyne probe, serially diluted as shown, and run on NuPAGE® Novex® 4-12% gels. Images (left panels) were obtained on the FLA-3000 scanner using 532 nm excitation. Gels were then post stained with SYPRO® Ruby stain and imaged using excitation at 473 nm (right panels). Detection sensitivity of the labeled proteins is less than 10 femtomoles. See, FIG. 7.

Example 7

Figure 8:
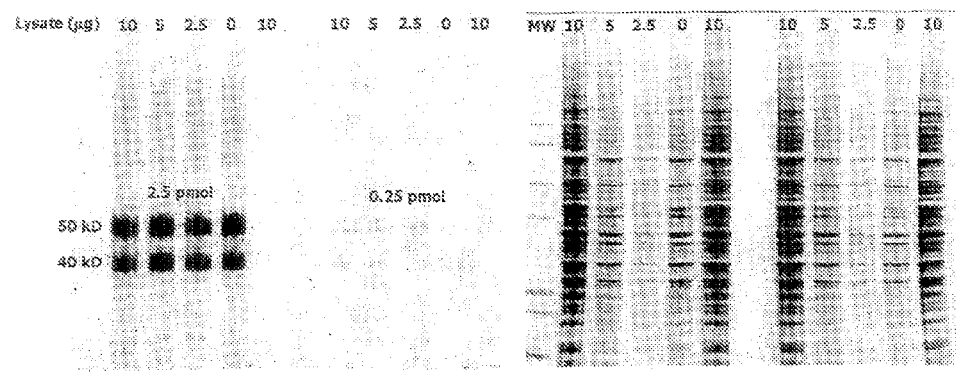
FIG. 8 shows that labeling efficiency of 40 and 50 kd azide-labeled, odel proteins is unchanged in complex protein extracts.

Labeling Efficiency of 40 and 50 kd Azide-Labeled Model Proteins is Unchanged in Complex Protein Extracts Either 100 ng (25 pmol) or 10 ng (2.5 pmol) each of azide-labeled 40 Kd & 50 Kd proteins were labeled with fluorescent alkyne probe as above in a background of either 100, 50, 25, or 0 µg of control Jurkat lysate (left panel). Note: 100 µg of control lysate was added after labeling to the '0 lysate' to facilitate recovery of the labeled protein by precipitation. The gel was post stained with SYPRO® Ruby total protein stain. See FIG. 8.

Example 8

Figure 9A:
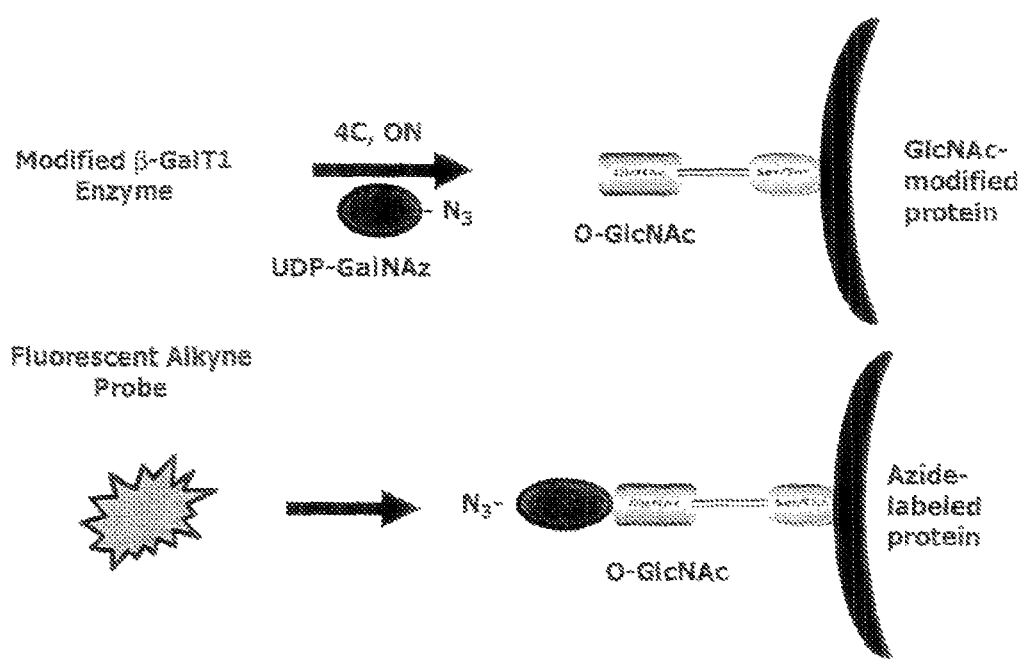
FIG. 9 shows the GalT1 enzymatic labeling and detection of a-crystallin O-GlcNAc A) schematically and B) detection after separation on a gel.
Figure 9B:
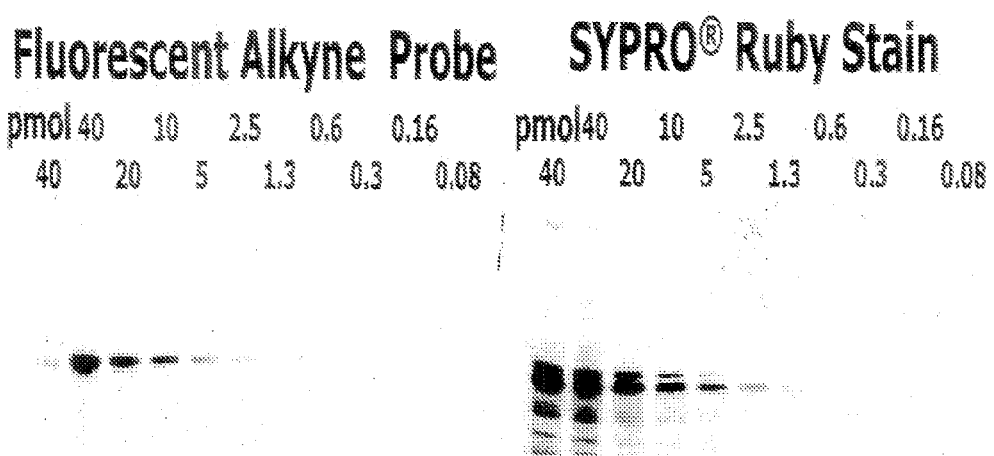

Enzymatic Labeling and Detection of α-crystallin O-GlcNAc

α-crystallin O-GlcNAc was enzymatically labeled with azide (UDP-GalNAz) using a modified b-GalT1 enzyme. The protein was subsequently reacted with a fluorescent alkyne probe as described. The proteins were run on 1-D NuPAGE® Novex® 4-12% gels at the dilutions shown. Note: Only 2-10% of α-crystallin is O-GlcNAc-modified and therefore the detection sensitivity of the O-GlcNAc moiety is in the mid-to-low femtomole range (10-45 fmols). See FIG. 9.

Example 9

Comparison of GalT1 Enzyme Labeling with a-O-GlcNAc Monoclonal Antibody CTD 110.6

Figure 10:
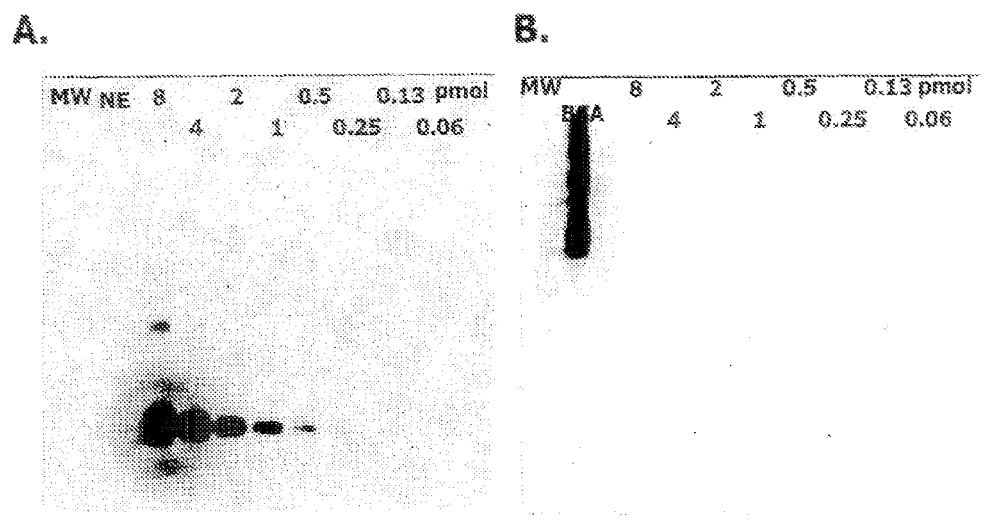
FIG. 10 shows a comparison of GalT1 enzymatic labeling and Click-iT detection of α-crystallin O-GlcNAc to detection with the O-GlcNAc Monoclonal Antibody CTD 110.6.

In A., α-crystallin O-GlcNAc was enzymatically labeled with the modified GalT1 enzyme and subsequently reacted with a biotin-alkyne probe. The proteins were run on 1-D NuPAGE® Novex® 4-12% Bis-Tris gels, at the dilutions shown, and blotted onto PVDF membrane. The PVDF membrane was then incubated in streptavidin-HRP and proteins were detected using ECL Plus™ (GE Biosystems). Lane 2 (NE) represents the 8 pmoL no-enzyme added control. Note: In A, the detection sensitivity of O-GlcNAc by Western blot is in the low femtomole range (3-10 finols). In B., untreated α-crystallin was run on 1-D gels and blotted as described above. The PVDF membrane was processed using the O-GlcNAc Western Blot Detection Kit (Pierce) according to manufacturer's instructions. The kit utilizes the CTD 10.6 α-O-GlcNAc monoclonal antibody. Lane 2 contains 5 ng of the positive control (O-GlcNAc-modified BSA) provided in the kit. No α-crystallin is detected using the antibody detection system. See FIG. 10.

Example 10

Figure 11:
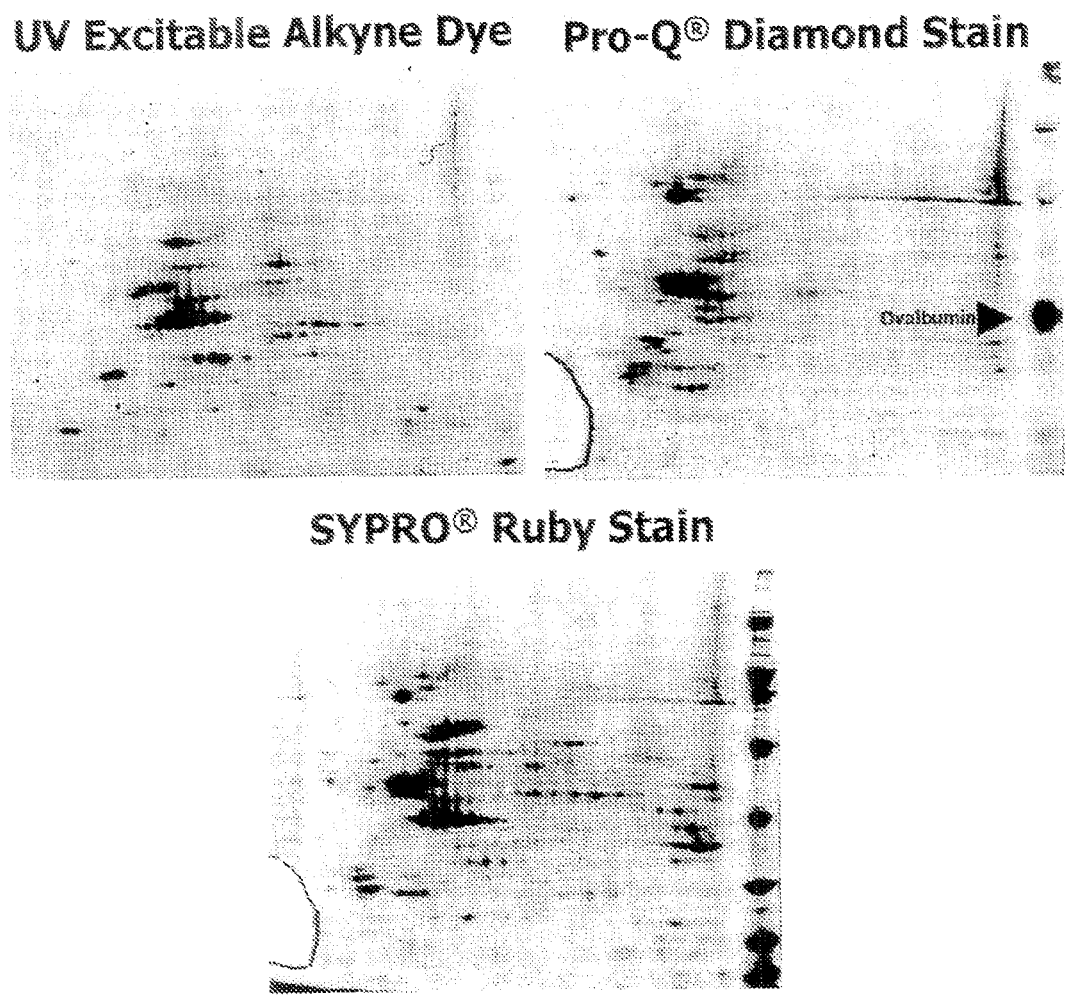
FIG. 11 shows the multiplex detection of O-GlcNAc modified proteins, phosphoproteins and total proteins in the same 2-D gel.

Multiplex Detection of O-GlcNAc Proteins, Phosphoproteins and Total Proteins in the Same 2-D gel Soluble extracts from Ac$_4$GlcNAz-fed Jurkat cells were labeled with UV excitable alkyne dye for 2 hours. The chloroform/methanol precipitated proteins were run on 2-D gels as described previously. The gel was rinsed in water and imaged with UV transillumination and 600/bp emission on a Lumi-Imager™ (Roche). The gel was then stained with Pro-Q® Diamond phosphoprotein stain, imaged with 532 nm excitation/580 LP emission on a FLA-3000 laser imager, stained with SYPRO® Ruby total protein stain, and imaged again with 473 nm excitation and 580 nm longpass emission according to the manufacturer's instructions. See FIG. 11.

Example 11

Multiplexed Western Blot Detection of O-GlcNAc Modified Proteins and Cofilin

Figure 12:
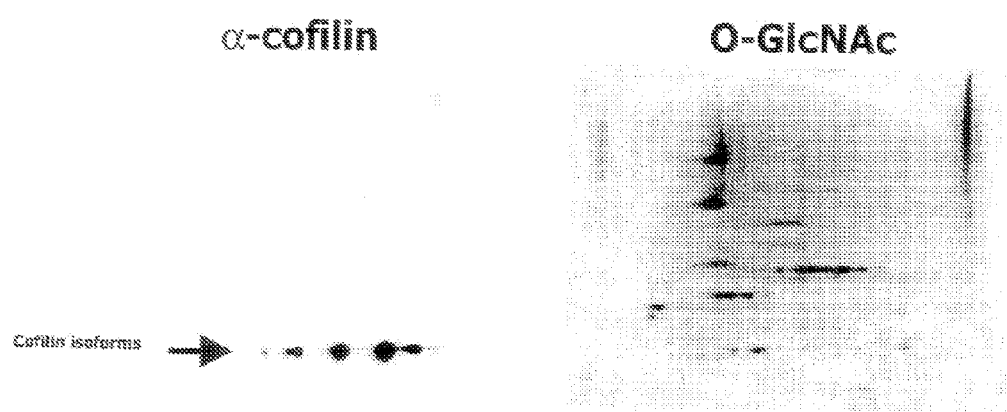
FIG. 12 shows multiplexed western bot detection of O-GlcNAc modified proteins and cofilin on the same membrane.

25 µg of soluble Jurkat cell proteins were run on 2-D gels as described and blotted onto PVDF membrane. The PVDF membrane was incubated in α-cofilin polyclonal Ab and detected with GAR-HRP secondary Ab with ECL Plus™ detection (GE Biosystems). After imaging, the blot was incubated in streptavidin AP and O-GlcNAc proteins were detected using the WesternBreeze® chemiluminescent detection kit (Invitrogen). See FIG. 12.

Example 12

Figure 13:
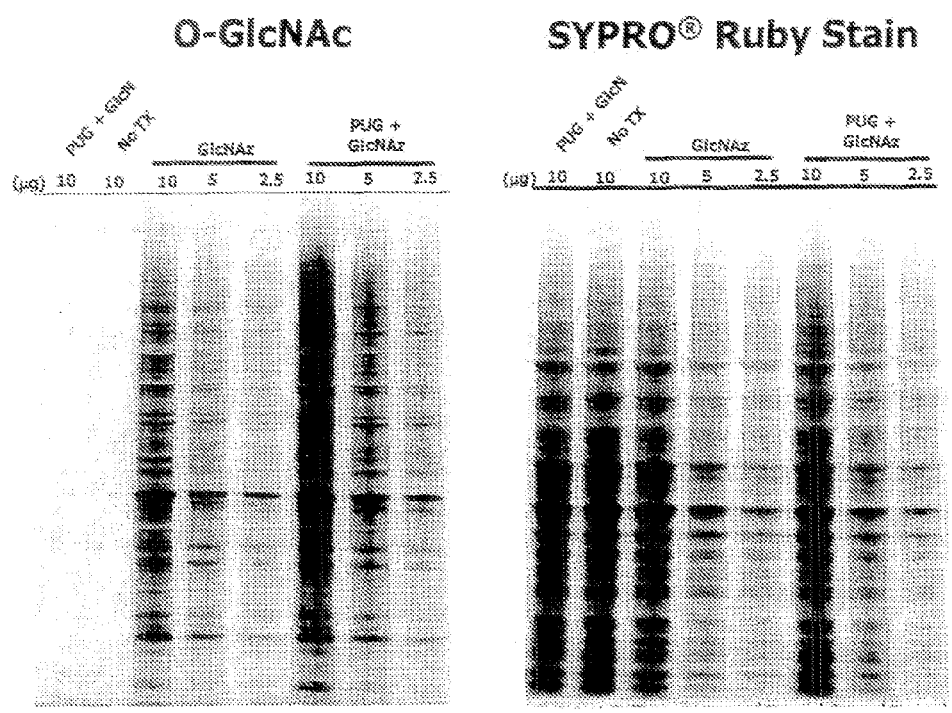
FIG. 13 shows the differential detection of O-GlcNAc modified proteins in control and O-GlcNAcase inhibitor (PUGNAc)-treated cultured cell extracts.

Differential Detection of O-GlcNAc Modified Proteins in Control and Inhibitor-Treated Cultured Cell Extracts Jurkat cells cultured overnight with Ac$_4$GlcNAz with and without PUGNAc treatment. PUGNAc is a commonly used inhibitor of O-GlcNAcase. Soluble Jurkat lysate preparations were labeled with fluorescent alkyne. Lane 1) cells treated with 50 µM PUGNAc and 4 mM glucosamine 3 hrs prior to harvest; Lane 2) no treatment; Lanes 3-5) cells cultured overnight with 250 µM Ac$_4$GlcNAz; Lanes 6-8) cells cultured overnight with 250 µM Ac$_4$GlcNAz then treated with 50 µM PUGNAc and additional 250 µM Ac$_4$GlcNAz 3 hrs prior to harvest. Proteins treated with PUGNAc (lanes 6-8) show a marked increase in O-GlcNAc staining over the untreated controls (lanes 3-5). See FIG. 13.

Example 13

In-gel Ligation of Glycoproteins

Figure 18:
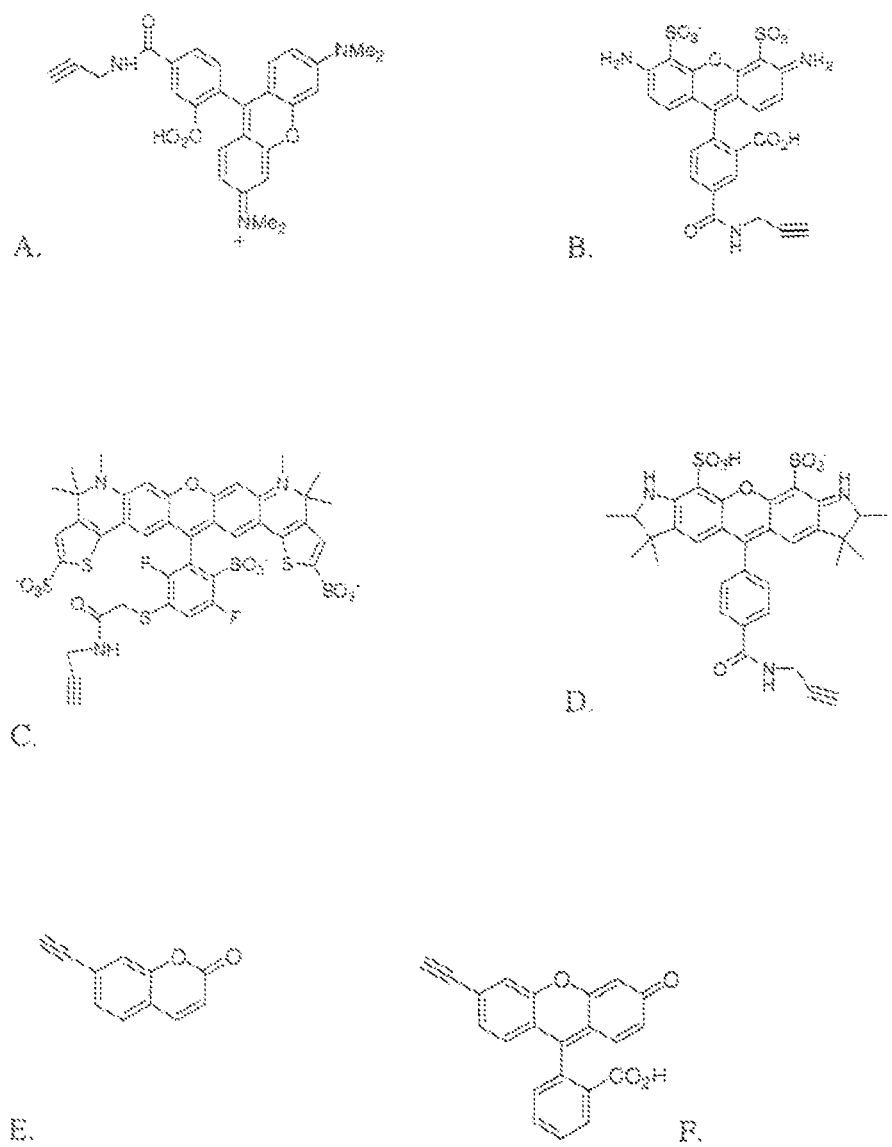
FIG. 18 shows structures of four present (A-D) and two potential (E,F) alkyne fluorophores that can be used to label biomolecules using the methods of the invention: A) TAMRA-alkyne; B) Alexa 488-Alkyne; C) Alexa 633-Alkyne; D) Alexa 532-Alkyne, E) a potential fluorogenic alkyne; F) a potential fluorogenic alkyne.

Fluorescent alkyne compounds for use in in-gel ligation are shown in FIG. 18 (A-D). Additionally, 2 potential fluorogenic alkynes are shown in E and F. The TAMRA-alkyne compound, shown in the upper left-hand frame, was used in in-gel staining experiments whereby azido groups were incorporated into proteins in vitro using a reactive azido-succinimidyl ester, or in vivo, by feeding cells azido-modified sugars.

Cell lysates were obtained from cultured Jurkat cells that were fed azido-modified sugars.

Azide-Alkyne Reaction Conditions for In-Gel or Western Blot Detection:

| Component | Volume | Final |
|---|---|---|
| Protein in 1% SDS, 50 mM Tris pH8 | 50 uL | 100-200 ug |
| Tris-HCl, pH 8.0 (1M) | 7.5 uL | 50 mM |
| Propylene glycol | 50 uL | 25% |
| $CuSO_4$ (50 mM) | 4 uL | 1 mM |
| DMSO, 0.5M | 4 uL | 10 mM |
| H20 | 62.5 uL | to 200 uL |
| Alkyne compound 1 mM (eg TAMRA or biotin) | 2 uL | 10 uM |
| Na Ascorbate (100 mM) | 10 uL | 5 mM |

All components are combined, adding the ascorbate last and the solution is vortexed gently, with a final solution volume of 200 uL. 10 uL of 100 mM BCS is added (solution turns orange if CuI is present) and vortexed gently followed by a layer of argon. The solution is mixed on rotator at room temperature for 1 hour.

After the reaction, the protein is precipitated out using the following protocol. 600 μL of MeOH is added to the reaction mixture and vortexed 20 secs, (freeze 30 min if protein amount. is low), followed by 200 μL chloroform and vortexing 20 secs, then 450 μL $H_2O$ vortex 20 secs. The solution is spun @ 18 Kxg for 5 min. The upper phase is removed and 450 μL of MeOH is added followed by vortexing for 20 secs and spinning @ 18 Kxg for 5 min. The supernatant is removed and discarded. Finally, 600 μL of MeOH is added, vortex, and briefly sonicate to disperse pellet, followed by spinning @ 18 Kxg for 5 min.

For sodium ascorbate dilution to 100 mM, dry sodium ascorbate (5 mg) is combined with 250 μL $H_2O$.

Figure 19:
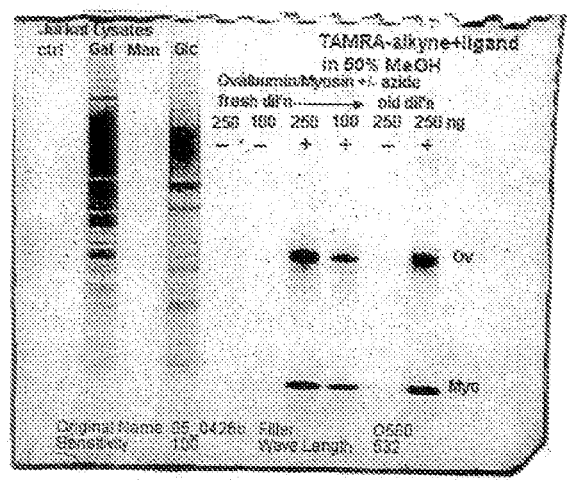
FIG. 19 shows the results of in-gel staining using the TAMRA-alkyne compound shown in FIG. 12A. Lanes 2, 3, and 4 on the left side of the gel represent cellular extracts that were labeled with azide-modified sugars: lane 1 is the control, non-labeled cells. On the right, control azide labeled proteins (ovalbumin and myoglobin) (+) or non-labeled controls (−) are shown at varying concentrations. The results show very efficient and selective in-gel labeling of azido-modified proteins.

FIG. 19, shows the results of electrophoresis of proteins labeled with the TAMRA-Alkyne compound using the protocol provided. Lanes 2, 3, and 4 on the left side of the gel represent cellular extracts that had incorporated azide-modified sugars, lane 1 is the control, non-azide sugar fed cells. On the right, control azide labeled proteins (ovalbumin and myoglobin) (+) or non-labeled controls (−) are shown at varying concentrations. The results show very efficient and selective in-gel detection of azido-modified proteins.

Example 14

Figure 14A:
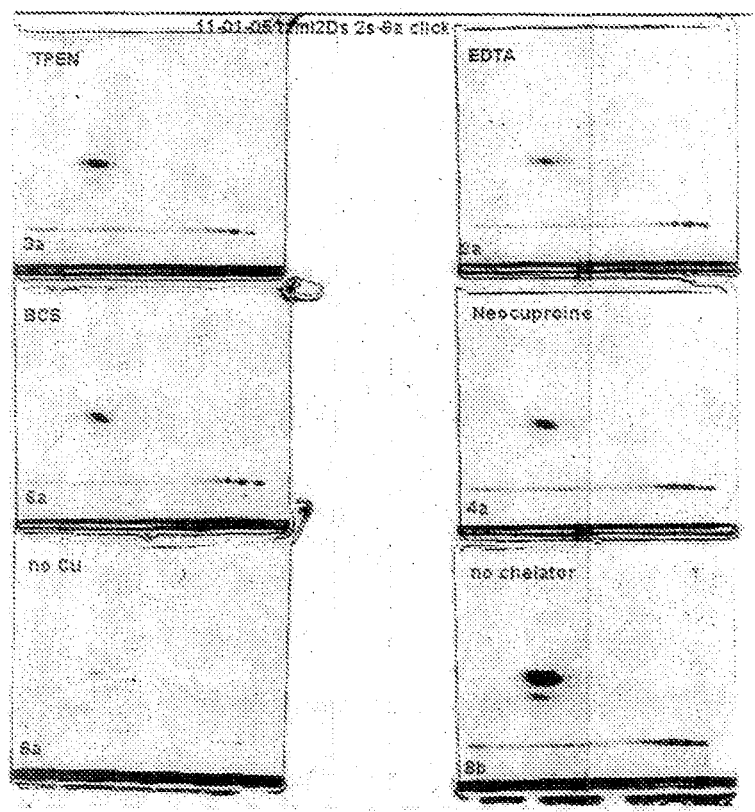
FIG. 14 depicts gels showing the results of separating proteins labeled using the click reaction with different chelators. 2.5 µg each of azido-ovalbumin and azido-myoglobin spiked into 80 ug of unlabeled Jurkat lysate was labeled with TAMRA alkyne for 2 hrs. The reaction contained 50 mM TRIS pH8, 25% propylene glycol, 1 mM $CuSO_4$, 5 mM sodium ascorbate, 20 uM TAMRA alkyne. The reactions were performed with and without chelator (10 mM TPEN [upper left gel], EDTA [upper right gel], bathocuproine disulfonic acid (BCS) [middle left gel] or neocuproine [middle right gel]). Control reactions were performed without $CuSO_4$ [lower left gel] or without chelator [lower right gel]. After labeling, the samples were precipitated, resolubilized in 7 mM urea/2 mM thiourea/65 mM DTT/2% CHAPS/ and approximately 30 µg was analyzed on 2-D gels (pH 4-7 IEF strips, 4-12% BIS-TRIS gels with MOPS buffer). The TAMRA signal was imaged at 532 nm excitation, 580 long pass emission on a Fuji FLA3000 (14A) then the gels were post-stained with Sypro® Ruby total protein gel stain (14B).
Figure 14B:
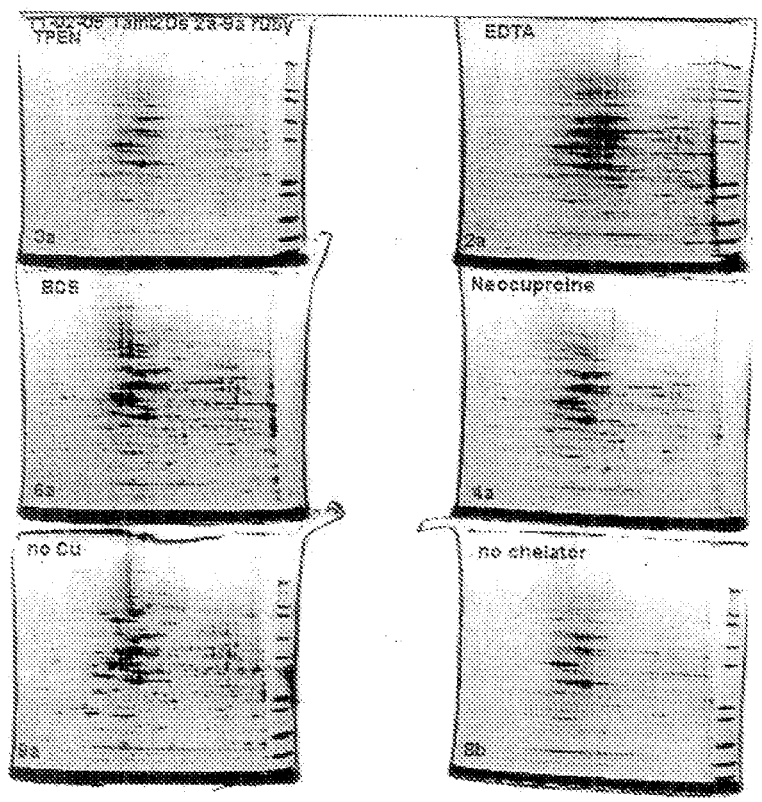

2.5 μg each of azido-ovalbumin and azido-myoglobin were spiked into 80 ug of unlabeled Jurkat lysate. The lysate was then labeled with TAMRA alkyne for 2 hrs. The reaction contained 50 mM TRIS pH8, 25% propylene glycol, 1 mM $CuSO_4$, 5 mM sodium ascorbate, 20 uM TAMRA alkyne. The reactions were performed with and without a chelator (10 mM of either TPEN, EDTA, bathocuproine disulfonic acid (BCS) or neocuproine). The control reaction was performed without $CuSO_4$. After labeling, the samples were precipitated, resolubilized in 7 mM urea/2 mM thiourea/65 mM DTT/2% CHAPS/ and approximately 30 μg of each sample was analyzed on 2-D gels (pH 4-7 IEF strips, 4-12% BIS-TRIS gels with MOPS buffer). The TAMRA signal was imaged at 532 nm excitation, 580 long pass emission on a Fuji FLA3000 then the gels were post-stained with SYPRO® Ruby total protein gel stain (FIG. 14A). The results show that addition of chelator greatly improves the resolution of the protein separation. bathocuproine disulfonic acid (BCS), a Cu I chelator, gives the best results. See total protein stain, FIG. 14B.

Figure 15A:
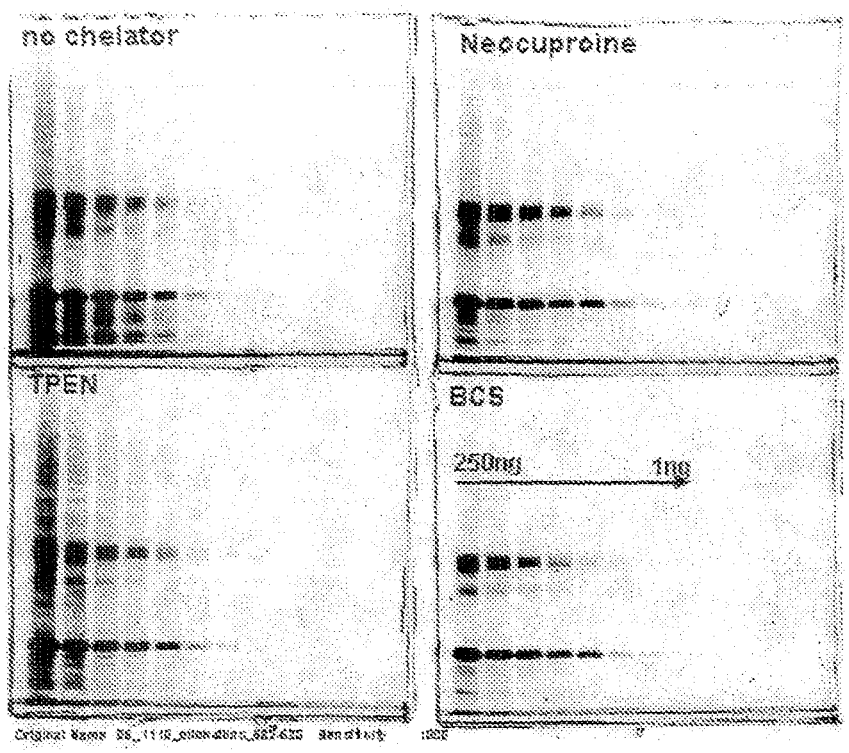
FIG. 15A shows that the chelators reduce the background of the image for the TAMRA signal without compromising sensitivity.
Figure 15B:
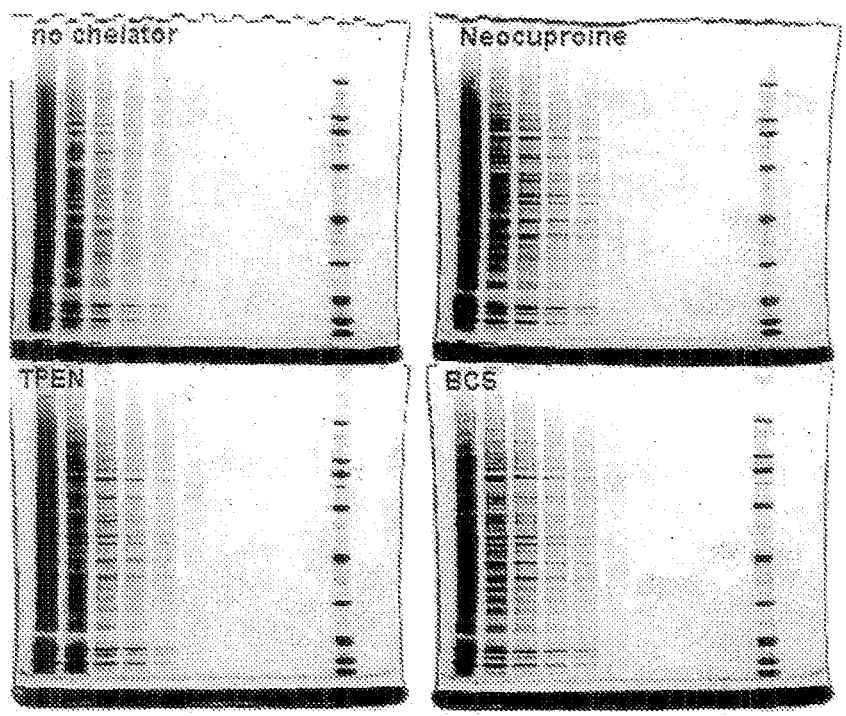
In FIG. 15B, post-staining with Sypro® Ruby total protein gel stain shows that the band resolution is much better for the samples with chelator.

In a second experiment, the samples and click labeling conditions were the same, except that chelator treatments included the addition of either 5 mM TPEN, BCS, or Neocuproine at the beginning of the reaction. After labeling, the samples were precipitated, resolubilized in LDS buffer+5 mM TCEP and serial 2-fold dilutions were performed. Dilutions were loaded onto 4-12% BIS-TRIS gels with MOPS running buffer (250 ng each of ovalbumin and myglobin in lane 1). FIG. 15 A shows that the chelators reduce the background of the image for the TAMRA signal without compromising sensitivity. In FIG. 15B, post-staining with Sypro® Ruby total protein gel stain shows that the band resolution is much better for the samples with chelator.

Figure 16:
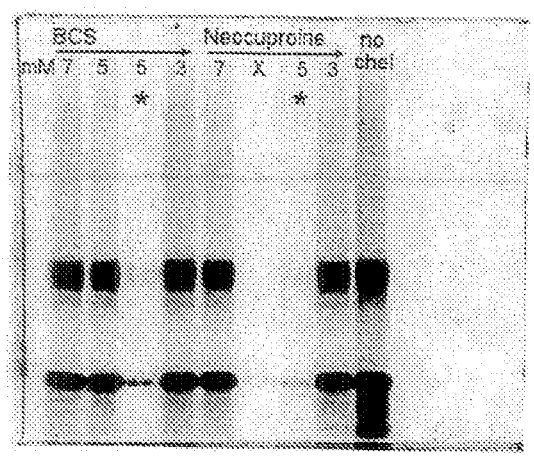
FIG. 16: The samples and click labeling conditions are the same as for FIG. 14, except that chelator treatments include addition of either 7 mM, 5 mM or 2 mM BCS or neocuproine. The lanes marked with an asterisk in (A) indicate reactions in which the $CuSO_4$ and BCS were added to the reaction and vortexed prior to adding the sodium ascorbate. In all other reactions the $CuSO_4$ and sodium ascorbate were added and vortexed prior to adding the BCS. The gels show that it is imperative to add the sodium ascorbate and $CuSO_4$ to the reaction tube and mix prior to adding the chelator. If the chelator and $CuSO_4$ are added and vortexed prior to adding the sodium acorbate, the azide-alkyne labeling does not proceed, suggesting that the chelator inhibits the reduction of Cu II to Cu I.
Figure 16:
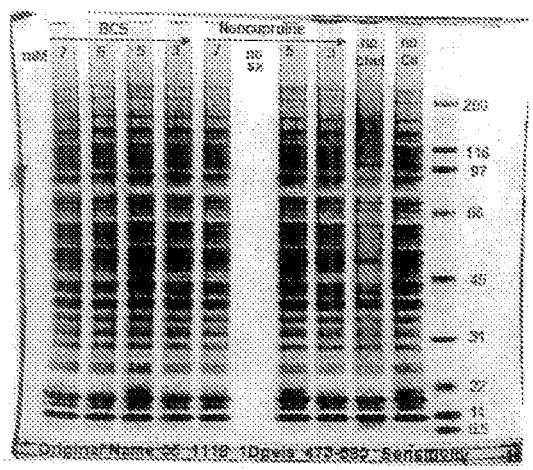

A further experiment testing the effect of chelators used the same click labeling conditions except that the chelator treatments included addition of either 7 mM, 5 mM, or 2 mM BCS; or 7 mM, 5 mM, or 2 mM neocuproine. The lanes marked with an asterisk in FIG. 16 indicate reactions in which the CuSO4 and BCS were added to the reaction and vortexed prior adding the sodium ascorbate. In all other reactions the CuSO4 and sodium ascorbate were added and vortexed prior to adding the BCS. The gels show that it is imperative to add the sodium ascorbate and CuSO4 to the reaction tube and mix prior to adding the chelator. If the chelator and CuSO4 are added and vortexed prior to adding the sodium acorbate, the azide-alkyne labeling does not proceed, suggesting that the chelator inhibits the reduction of Cu (II) to Cu (I).

Example 15

Enzymatic Labeling of Antibodies Using Click Chemistry

Figure 17A:
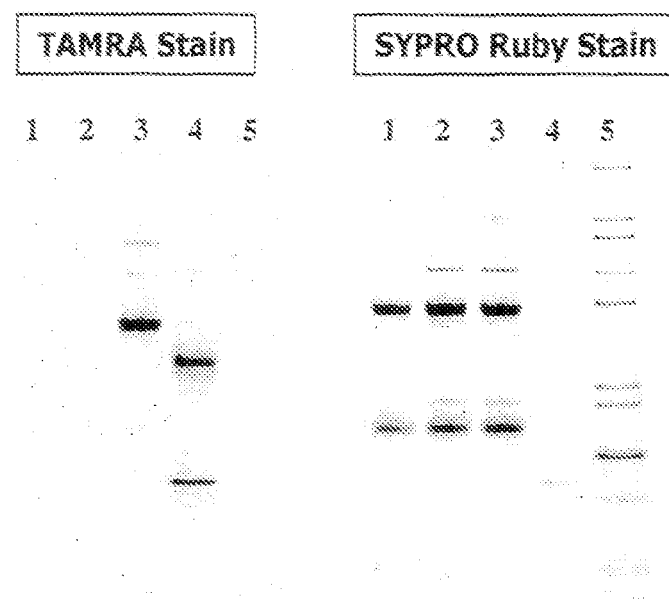
FIG. 17 shows the enzymatic labeling of antibodies using click chemistry: A) Lane 1—Goat antibody only (GAb); Lane 2—GAb with GalT1 enzyme but without UDP-GalNAz Control; Lane 3—GAb with enzyme and UDP-GalNAz. Lane 4—azide-labeled ovalbumin and myoglobin control proteins; Lane 5—MW markers unlabeled and B) Azide-labeled goat antibodies (from above) were run as a dilution series followed by post-staining with SYPRO Ruby gel stain to show total protein pattern.
Figure 17B:
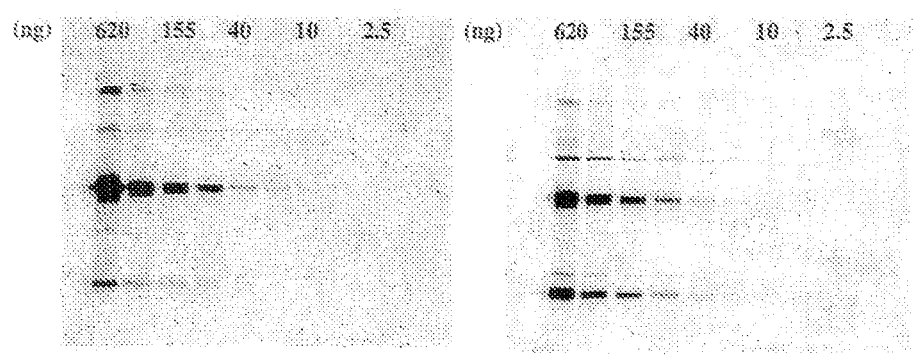

Goat IgG antibodies were reduced and alkylated, then deglycosylated in 2 separate aliquots using Endo H enzyme. Deglycosylated antibodies (2 separate preps) were then labeled with GalNAz using 33 ng/uL Gal T1 Y289L enzyme and 500 uM UDP GalNAz (0.5 ug/uL goat antibody) in a 150 uL reaction. Reactions were incubated at 4 degrees C overnight. 4-500 ng of goat antibody (treated as listed on gel; either no-GalNAz control or azide labeled) was loaded into each lane of a 4-12% Bis Tris gel. Electrophoresis was performed at 200v for ~50 min. using MES buffer. Gels were stained with TAMRA-alkyne stain and imaged on the Fuji imager at 532 nm (excitation) and 580 nm emission. Gels were poststained with SYPRO Ruby using the overnight protocol. See FIG. 17.

U.S. patent applications with attorney docket numbers IVGN 745 and IVGN 745.1 all filed on Feb. 12, 2007, claiming priority to U.S. Provisional Application Nos. 60/772,221 and 60/804,640 are hereby incorporated by reference.

The entirety of each patent, patent application, publication and document referenced herein hereby is incorporated by reference in their entirety, including all tables, drawings, and figures. All patents and publications are herein incorporated by reference to the same extent as if each was specifically and individually indicated to be incorporated by reference. Citation of the above patents, patent applications, publications and documents is not an admission that any of the foregoing is pertinent prior art, nor does it constitute any admission as to the contents or date of these publications or documents.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described.

Modifications may be made to the foregoing without departing from the scope, spirit and basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. One skilled in the art readily appreciates that the present invention is well adapted to carry out the objects and obtain the ends and advantages mentioned, as well as those inherent therein. The examples provided herein are representative of specific embodiments, are exemplary, and are not intended as limitations on the scope of the invention.

The invention illustratively described herein suitably may be practiced in the absence of any element(s) not specifically disclosed herein. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention claimed is:

1. A method of producing a glycomodified protein, comprising
attaching an azido-modified galactose to a GlcNAc residue on a first protein having a GlcNAc-GlcNAc linkage; and
mixing said first protein, having attached thereto said azido-modified galactose with a reporter molecule, carrier molecule or solid support capable of reacting with the azide group of said azido-modified galactose;
wherein said azido-modified galactose is N-azidoacetylgalactosamine (GalNAz) and said reporter molecule, carrier molecule or solid support is labeled with an alkyne or an activated alkyne group;
wherein said reporter molecule, carrier molecule or solid support attaches to the first protein at the azide group of said attached azido-modified galactose through the alkyne or the activated alkyne group, thereby forming the glycomodified protein; and
wherein said attaching of the azido-modified galactose (GalNAz) is carried out by an enzymatic attachment step utilizing a mutant β-1,4-galactosyl transferase enzyme (Y289L GalT1) and UDP-GalNAz as a substrate, which transfers said azido-modified galactose (GalNAz) from said UDP-GalNAz to said GlcNAc residue of said first protein.

2. The method of claim 1, wherein said first protein is an antibody.

3. The method of claim 1, wherein prior to the attaching step, the method comprises cleaving an oligosaccharide present on a first protein at a GlcNAc-GlcNAc linkage to obtain a protein comprising a GlcNAc residue.

4. The method of claim 3, wherein said oligosaccharide is cleaved using endoglycosidase H cleavage at the GlcNAc-GlcNAc linkage.

5. The method of claim 1, wherein said first protein is derived from a non-human source.

6. The method of claim 5, wherein said glycomodified protein is humanized.

7. The method of claim 3, wherein said oligosaccharide is cleaved using endoglycosidase M cleavage at the GlcNAc-GlcNAc linkage.

8. The method of claim 1, wherein the attaching step is in a solution substantially free of proteases.

9. The method of claim 1, wherein said reporter molecule is selected from the group consisting of a fluorescent dye, an enzyme, a radiolabel, a metal chelator, and a detectable substrate.

10. The method of claim 1, wherein said carrier is selected from the group consisting of therapeutic agents, DNA, protein, peptides, and sugars.

* * * * *